United States Patent [19]

Scheeren et al.

[11] Patent Number: 5,294,701
[45] Date of Patent: * Mar. 15, 1994

[54] ANTHRACYCLINE COMPOUNDS AND INTERMEDIATES

[75] Inventors: Johan W. Scheeren, Malden; Joannes F. M. de Bie, Nijmegen; Dirk de Vos, Oegstgeest, all of Netherlands

[73] Assignee: Pharmachemie B.V., Haarlem, Netherlands

[*] Notice: The portion of the term of this patent subsequent to Jan. 7, 2009 has been disclaimed.

[21] Appl. No.: 879,737

[22] Filed: May 6, 1992

Related U.S. Application Data

[62] Division of Ser. No. 746,453, Aug. 16, 1991, abandoned.

[30] Foreign Application Priority Data

Aug. 16, 1990 [NL] Netherlands .................. 9001834

[51] Int. Cl.$^5$ .................. C07H 15/24; C07D 221/18
[52] U.S. Cl. .................. 536/6.4; 546/77; 546/78; 552/201; 552/202; 552/208; 552/209; 552/261; 552/262; 552/271; 552/272
[58] Field of Search ............ 536/6.4, 6.5; 514/34; 546/77, 78; 552/201, 202, 208, 209, 261, 262, 271, 272

[56] References Cited

U.S. PATENT DOCUMENTS

| | | | |
|---|---|---|---|
| 4,564,674 | 1/1986 | Terashima et al. | 536/6.4 |
| 4,973,674 | 11/1990 | Brasca et al. | 536/6.4 |
| 5,079,349 | 1/1992 | Scheeren | 536/6.4 |

*Primary Examiner*—Johnnie R. Brown
*Assistant Examiner*—Elli Peselev
*Attorney, Agent, or Firm*—Browdy and Neimark

[57] ABSTRACT

This invention provides novel anti-tumour compounds of the formula

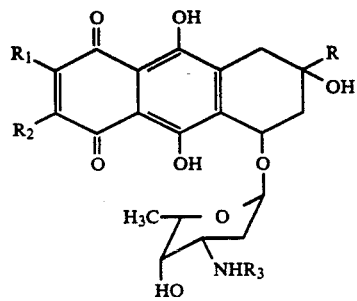

wherein $R_1$ and $R_2$ are hydrogen or together form an alkyl-, alkoxy- or OH-substituted aromatic group, which optionally contains an N atom as a hetero-atom; R is —COCH$_3$ or —C≡C—R$_4$ and R$_4$ is H or trimethylsilyl; and R$_3$ is H or —COCF$_3$; and acid addition salts thereof; as well as compositions containing these compounds.

15 Claims, No Drawings

ANTHRACYCLINE COMPOUNDS AND INTERMEDIATES

This application is a divisional of application Ser. No. 07/746,453, filed Aug. 16, 1991, now abandoned.

Daunomycin and adriamycin have been known as anti-neoplastic (and also as antibiotic) compounds for many years.

X=H: daunomycin
X=OH: adriamycin

The invention provides novel compounds having anti-tumour activity, i.e. compounds according to formula 1 wherein
R is —COCH$_3$ or —C≡C—R$_4$;
R$_4$ is H or —Si(CH$_3$)$_3$;
R$_1$ and R$_2$ are H or together form a group —CR$_5$=C-R$_6$—CR$_7$=CR$_8$, —CR$_9$=CR$_{10}$—CR$_{11}$=N— or —N=CR$_9$—CR$_{10}$=CR$_{11}$;
each of the symbols R$_5$, R$_6$, R$_7$ and R$_8$ represents H, a C$_1$-C$_3$ alkyl group, a C$_1$-C$_3$ alkoxy group or a —OH group;
each of the symbols R$_9$, R$_{10}$ and R$_{11}$ represents H or a C$_1$-C$_3$ alkyl group; and
R$_3$ is H or —COCF$_3$;
as well as acid addition salts thereof;
with the exclusion of the compounds wherein R$_1$ and R$_2$ form a group —CH=CH—CH=C(OC$_1$-C$_3$ alkyl)— or —CH=CH—CH=C(OH)— or —C(OCH$_3$)=CH—CH=C(OCH$_3$)— or —CH=C(OCH$_3$)—C(OCH$_3$)=CH—, R is a group —COCH$_3$ and R$_3$ is H, or, when R$_1$ and R$_2$ form a group —CH=CH—CH=C(OH)— or a group —CH=CH—CH=C(OCH$_3$)—, a group —COCF$_3$; and acid addition salts of these compounds;
and the compounds wherein R$_1$ and R$_2$ form a group —CH=CH—CH=CH—, —CH=C(CH$_3$)—C(CH$_3$)=CH— or —C(CH$_3$)=CH—CH=C(CH$_3$)—, R is a group —COCH$_3$ and R$_3$ is H or, when R$_1$ and R$_2$ form a group —CH=CH—CH=CH—, a group —COCF$_3$;
and acid addition salts of these compounds.

This invention comprises both the separate stereoisomers and mixtures thereof, including racemic mixtures and mixtures of diastereoisomers.

Dutch patent application 7600075 discloses stereo isomers of the HCl salt of 4-demethoxy daunomycin and the N-trifluoro acetate of 4-demethoxy daunomycin.

R = H or —COCF$_3$

Furthermore, Dutch patent application 7600075 mentions 1-methoxy daunomycin, 4-demethoxy-2,3-dimethoxy daunomycin and 4-demethoxy-1,4-dimethyl daunomycin and 4-demethoxy-2,3-dimethyl daunomycin, without disclosing physico-chemical properties, details for the preparation and pharmaceutical properties. The stereo isomers of 4-demethoxy daunomycin are also described in Anticancer Agents Based on Natural Product Models, edited by J. M. Cassady and J. D. Douros, Academic Press 1980, Chapter 1, The Development of New Antitumor Anthracyclines by Federico Arcamone. This publication also mentions the anti-tumour activity of the stereoisomers of 4-demethoxydaunomycin disclosed in Dutch patent application 7600075. Furthermore the latter reference mentions 4-demethoxy-1,4-dimethyldaunomycin and 4-demethoxy-2,3-dimethyldaunomycin as well as carminomycin (4-demethoxy-4-hydroxy-daunomycin) and their anti-tumour activity. 4-Demethoxy-4-ethoxydaunomycin and 4-demethoxy-4-isopropoxy-daunomycin and their anti-tumour activity are known from Anthracycline Antibiotics, Ed. by Hassan S. El Khadem, Ac. Press, 1982, N. Y., Chapter I, Anthracyclines in the National Cancer Institute Programme, M. Benton Naff, Jacqueline Plowman, V. L. Narayanan, 19 a.f.

DE-A-2,804,099 discloses N-trifluoroacetyl carminomycin and mentions the anti-tumour activity of this compound. U.S. Pat. No. 4,020,270 mentions N-trifluoroacetal daunomycin.

More specific examples of the novel compounds of the invention are:

compounds according to formula 2

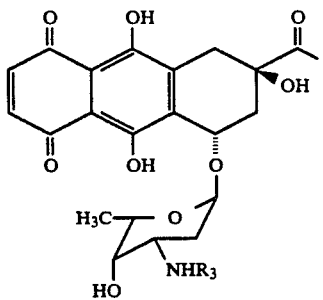

wherein $R_3$ is the defined as above, as well as salts thereof with an acid;
compounds according to formula 3

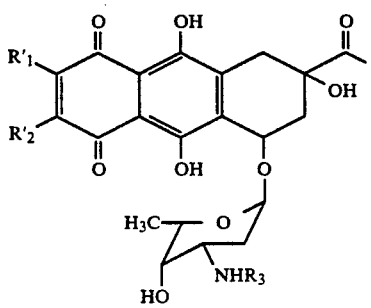

wherein $R'_1$ and $R'_2$ together form a group —CH=C(CH$_3$)—CH=N— or —N=CH—C(CH$_3$)=CH— and $R_3$ is as defined above; as well as salts thereof with an acid;
compounds according to formula 4

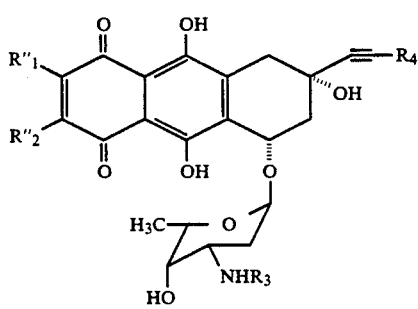

wherein $R''_1 = R''_2 = H$ or $R''_1$ and $R''_2$ together form a group —CH=CH—CH=C(OCH$_3$)— or —CH=CH—CH=CH— and $R_3$ and $R_4$ have the meanings stated in claim 1; as well as salts thereof with an acid; compounds according to formula 5

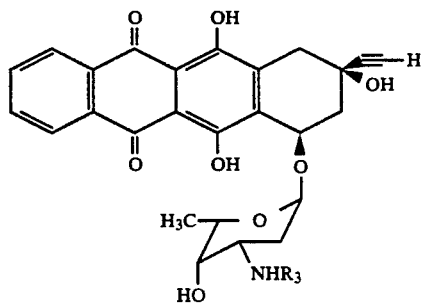

wherein $R_3$ is as defined in claim 1; as well as salts thereof with an acid.

Because of the anti-tumour activity the compound having the formula 6

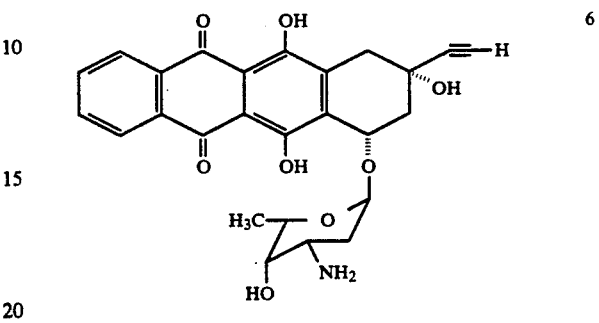

as well as the salts thereof with an acid are particularly preferred.

A number of compounds were examined with the following human tumour cell lines according to the method of R. van Lambalgen and P. Lelieveld, "The PIT method: and automated in vitro technique for drug toxicity testing", Invest. New Drugs 5, 161–165, 1987.

A 204 rhabdomyosarcoma (A-cells)
MCF-7 mammary carcinoma cells (M-cells)
T 24 bladder carcinoma cells (T-cells)
WiDr colon tumour cells (W-cells)
IgR-37 melanoma cells (Z-cells)

The cell lines where maintained in a continuous logarithmic culture in Dulbeco's medium supplemented with 10% fetal calf serum, penicillin (100 IU/ml) and streptomycin (100 µg/ml).

The following compounds where examined:

| Compound | Structure |
|---|---|
| HRM01 | Formula 18a |
| HRM03 | Formula 16a |
| HRM04 | Formula 17a |
| HRM10 | Formula 18b |
| HRM11* | Formula 52 |
| HRM12 | Formula 30a |
| HRM13 | Formula 41 |
| HRM15** | Formula 49 |
| HRM16 | Formula 40 |
| HRM09 | HCl salt of α-7.9-bis-epi-4-demethoxydaunomycin. Comparative compound |
| Daunomycin, HCl salt | Comparative compound |
| Adriamycin, HCl salt | Comparative compound |
| Etoposide*** | Comparative compound; conventional |

-continued

| Compound | Structure |
|---|---|
| | anti-tumour agent |

*1:1 mixture of the 7S, 9S and 7R, 9R isomers
**1:1 mixture of the 8S, 10S and 8R, 10R isomers
***Structure:

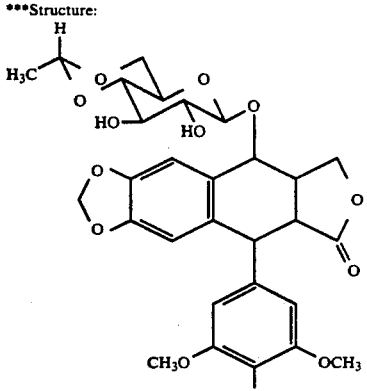

The ID$_{50}$ values of the above compounds, expressed in ng/ml, where determined according to the above-mentioned method of van Lambalgen and Lelieveld. The ID$_{50}$ value is the amount which inhibits 50% of the cell growth.

| Compounds | ID$_{50}$ values in ng/ml | | | | |
|---|---|---|---|---|---|
| | A204 | MCF-7 | T24 | WiDr | IgR-37 |
| HRM01 | 0.3 | 1 | 2 | 4 | 2 |
| HRM03 | 97 | 151 | 444 | 156 | 146 |
| HRM04 | 14 | 14 | 75 | 43 | 18 |
| HRM10 | 243 | 420 | 728 | 372 | 469 |
| HRM11 | 45 | 67 | 173 | 139 | 77 |
| HRM12 | 21 | 39 | 140 | 87 | 63 |
| HRM13 | 729 | 542 | 1047 | 1425 | 2441 |

| Compounds | ID$_{50}$ values in ng/ml | | | | |
|---|---|---|---|---|---|
| | A204 | MCF-7 | T24 | WiDr | IgR-37 |
| HRM15 | 171 | 334 | 949 | 779 | 459 |
| HRM16 | 280 | 338 | 1262 | 2116 | 1938 |
| Comparative compounds | | | | | |
| HRM09 | 302 | 745 | 1143 | 501 | 618 |
| Daunomycin.HCl | 1 | 1 | 4 | 3 | 1 |
| Adramycin.HCl | 4 | 6 | 18 | 16 | 6 |
| Etoposide | 91 | 187 | 457 | 624 | 427 |

N.B.: Because in mixtures of diastereoisomers generally one of the diastereoisomers is active and the other is not active or shows very little activity, the activity of the actually or most operative stereoisomer is for HRM11 and HRM15 considerably higher than indicated in the above table, because all compounds were of course examined in the same concentration.

From the above results it appears that some compounds of this invention show a higher activity than known compounds, while others have a lower activity. It is remarked thereto that there exists a need for both anti-tumour agents having a relatively weak activity and agents having a high activity: because anti-tumour agents can also attack healthy cells, less active anti-tumour agents are desirable under certain circumstances while on the other hand under different circumstances very active agents will be chosen. Furthermore, there is a continuous need for expanding the existing range of drugs against a specific disease, because in individual cases patients may respond unfavourably to the known drugs.

The present compounds can be synthesized according to several methods which are illustrated in the reaction schemes and preparation examples disclosed hereinafter. It is remarked that many of the intermediate compounds described hereinafter are novel compounds, e.g. the compounds of formulae 15a, 28a, 29a, 36a, 37a, 38, 39, 47, 48, 50, 51, 13a, 27, 33, 44 and 46; these novel compounds also form an aspect of this invention.

Reaction scheme A

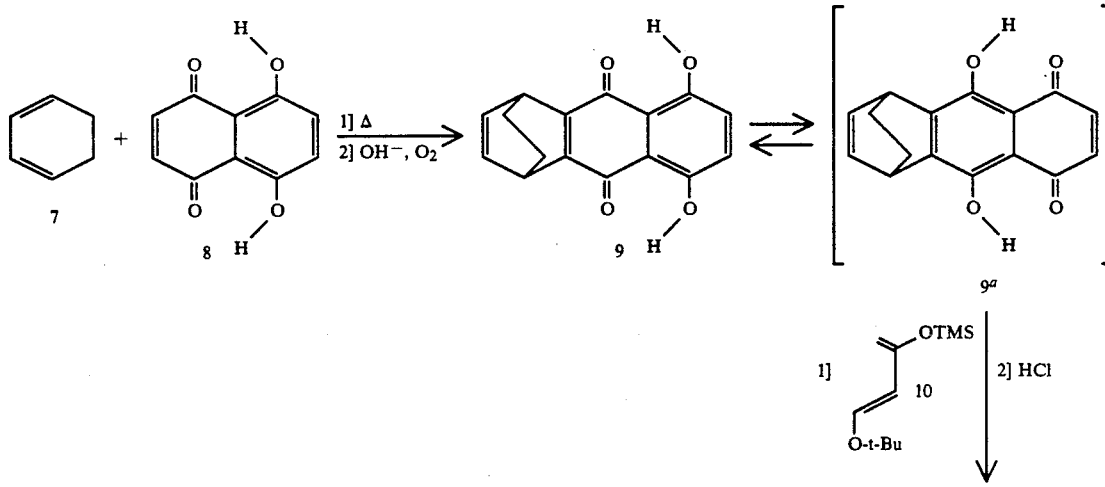

-continued
Reaction scheme A

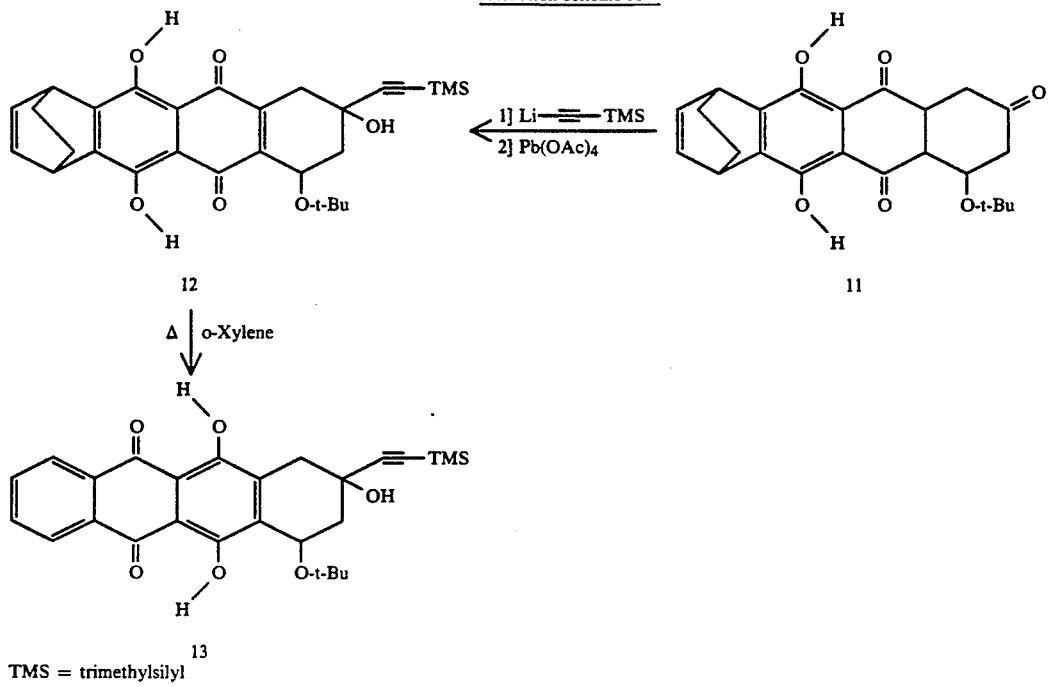

TMS = trimethylsilyl 1,4,9,10-tetrahydro-5,8-dihydroxy-9,10-dioxo-1,4-ethanoanthracene (9)

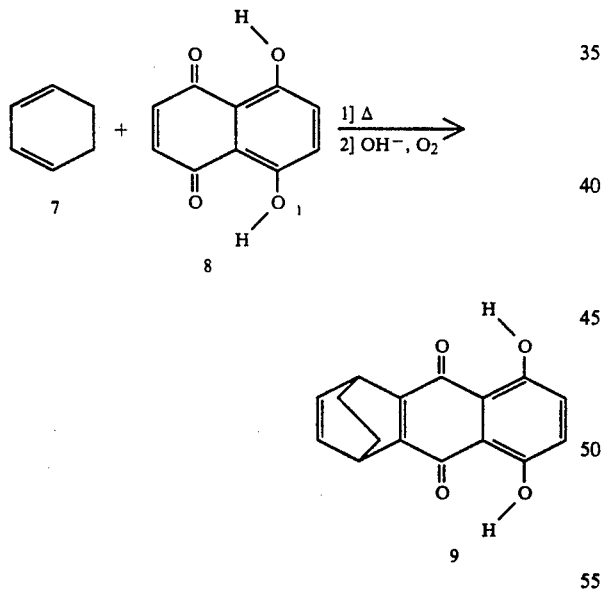

19.0 g (100 mmol) of pure naphthazarin (8) and 12.5 g (160 mmol) of 1,3-cyclohexadiene (7) were refluxed in 190 ml of THF for 5 days. The reaction was followed by means of TLC (ethyl acetate: n-hexane, 2:5). The colour of the solution changed from red to yellow/-brown. After evaporating, the product was purified by stirring the residue in 200 ml of petroleum ether 40/65 for one hour. The solid was filtered off and the yield was 23.8 g (88%).

The yellow compound was added to a solution of 20.0 g NaOH in 750 ml water while stirring. The solution was stirred for one hour while compressed air was passed through. The reaction was followed by means of TLC (ethyl acetate:n-hexane, 2:5). After the reaction 35 ml of concentrated HCl (37%) was added. The precipitated solid compound was filtered off. This red compound was rinsed from the filter with chloroform, whereafter the organic phase was washed with saturated sodium bicarbonate solution. After drying over anhydrous sodium sulphate and evaporating, 20.1 g (85%, overall 75%) of the compound (9/9a) could be isolated. Melting point 203°-204° C.

$^1$H-NMR (90 MHz, CDCl$_3$, TMS internal standard): δ=1.16-1.58 (4H, m, CH$_2$—CH$_2$), δ=4.49 ppm (2H, m, H$_1$ and H$_4$), δ=6.35 ppm (2H, dd, H—C≡C—H), δ=7.03 ppm (2H, s, ArH), δ=12.48 ppm (2H, s, ArOH).

1,4,6a,9,10,10a-hexahydro-5,12-dihydroxy-7-tert-butoxy-1,4-ethanonaphtacene-6,9,11-(10H)-trione (11)

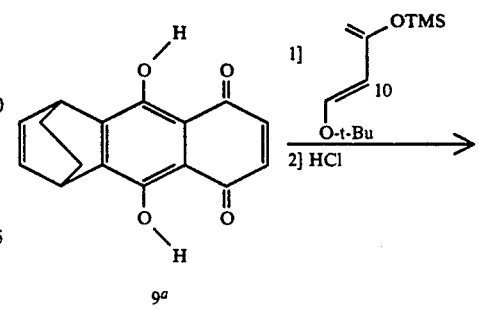

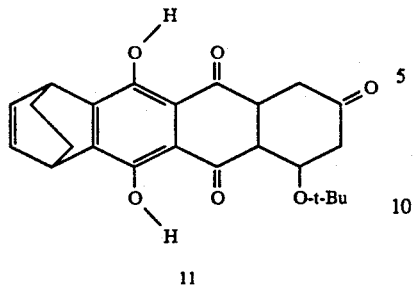

11

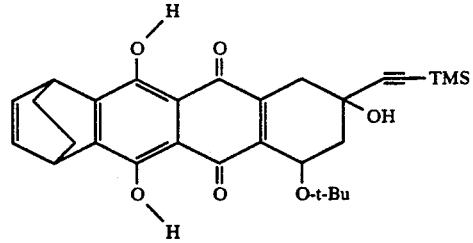

12

19.4 g (72 mmol) of (9/9a) was dissolved in 300 ml of toluene and placed under an argon atmosphere. 23.2 g (108 mmol, 1.5 eq.) of 1-tertbutoxy-3-trimethylsilyloxy-buta-1,3-diene (10) was added thereto. The course of the reaction was followed by means of TLC (ethyl acetate:n-hexane, 2:5). After stirring at room temperature for 5 days the reaction mixture was evaporated and taken up in 190 ml of cold THF (0° C.). 9.7 ml 1M HCl solution was added and the solution was stirred at 0° C. for 15 minutes. The course of the reaction was followed by means of TLC (ethyl acetate:n-hexane, 2:5). Then 500 ml of water was added and the aqueous layer was extracted with methylene chloride (2×500 ml). The organic layer was dried over anhydrous sodium sulphate and evaporated.

The product was purified by stirring the residue in 200 ml of diethylether for one night. The solid (pale yellow) was filtered off. The filtrate was evaporated and further purified by means of flash column chromatography (column 25 cm, 5 cm φ, eluent ethyl acetate:n-hexane, 2:3). The total yield was 22.2 g (75%). Melting point 154°-158° C.

$^1$H-NMR (90 MHz, CDCl$_3$, TMS internal standard):- (Mixture of endo and exo isomers) $\delta=0.7$ ppm (9H, s, C(CH$_3$)$_3$), $\delta=1.2$-1.61 ppm (4H, m, CH$_2$—CH$_2$), $\delta=2.1$-2.57 ppm (3H, H$_{10}$(ax)+H$_8$(eq)+H$_8$(ax)), $\delta=3.23$-3.6 ppm (3H, H$_{10a}$+H$_{6a}$+H$_{10}$(eq)), $\delta=4.39$ ppm (1H, m, H$_7$), $\delta=4.47$-4.63 ppm (2H, m, H$_1$+H$_4$), $\delta=6.45$ ppm (2H, dd, H—C≡C—H), $\delta=11.83$ ppm (1H, s, ArOH), $\delta=12.30$ ppm (1H, s, ArOH).

cis-9-trimethylsilylethynyl-1,4,7,8,9,10-hexahydro-6,9,11-trihydroxy-7-tert-butoxy-1,4-ethanonaphtacene-5,12-dione (12)

4.2 g (43 mmol) of trimethylsilyl acetylene was dissolved in 450 ml THF, which had been distilled over sodium, and thereafter an argon atmosphere was applied. The solution was cooled to $-78°$ C. and 26.2 ml (42 mmol) 1.6M n-butyl lithium was added. After stirring at $-78°$ C. for half a hour, 3.1 g (7.6 mmol) of 11 was added. The reaction mixture was stirred at $-78°$ C. for 3 hours, while the reaction was being followed by means of TLC (ethyl acetate:n-hexane, 2:5). At the end of the reaction the reaction mixture was permitted to warm-up slowly to room temperature and 150 ml of a 10% ammonium chloride solution was added. After 15 minutes 300 ml of water was added and the solution was twice extracted with 300 ml of chloroform. The collected organic fractions were dried over anhydrous sodium sulphate and evaporated after filtration. The residue was dissolved in 60 ml of glacial acetic acid and 3.4 g (7.7 mmol) of lead tetraacetate was added to the solution. After stirring for one night 200 ml of water was added. The red solid which precipitated, was removed by filtration and washed from the filter with 300 ml of chloroform. The solution was extracted with 75 ml of a saturated sodium bicarbonate solution. The organic phase was dried over anhydrous sodium sulphate, filtered and evaporated. The product was purified by means of a column separation (column 15 cm, 5 cm φ, eluent ethyl acetate:n-hexane, 1:4). The yield was 2.9 g (76%). Melting point 116°-118° C.

$^1$H-NMR (90 MHz, CDCl$_3$, TMS internal standard):- (Mixture of endo and exo isomers) $\delta=0.27$ ppm (9H, s, Si(CH$_3$)$_3$), $\delta=1.40$ ppm (9H, s, C(CH$_3$)$_3$), $\delta=1.20$-1.80 ppm (4H, m, CH$_2$—CH$_2$), $\delta=1.94$ ppm (1H, dd, J=14.5, Hz and J=3 Hz, H$_8$(ax)), $\delta=2.67$ ppm (1H, d, J=14.5 Hz, H$_8$(eq)), $\delta=3.04$ ppm (1H, d, J=17.5 Hz, H$_{10}$(ax)), $\delta=3.55$ ppm (1H, d, J=17.5 Hz, H$_{10}$(eq)), $\delta=4.63$ ppm (2H, m, H$_1$+H$_4$), $\delta=5.27$ ppm (1H, m, H$_7$), $\delta=5.72$ ppm (1H, s, OH), $\delta=6.48$ ppm (2H, dd, H—C≡C—H), $\delta=12.95$ ppm (1H, s, ArOH), $\delta=13.12$ ppm (1H, s, ArOH).

cis-9-trimethylsilylethynyl-7,8,9,10-tetrahydro-6,9,11-trihydroxy-7-tert-butoxynaphtacene-5,12-dione (13)

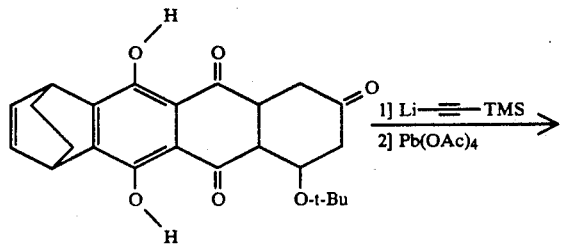

11

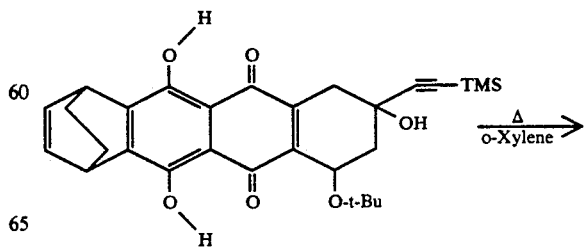

12

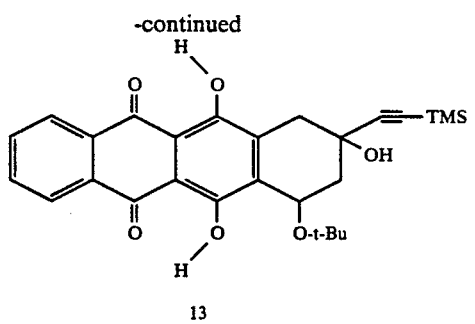

2.9 g (5.7 mmol) of (12) was dissolved in 30 ml of o-xylene. The solution was refluxed at 150° C. for 5 hours. The solution was evaporated and taken up in 30 ml of ether. The ether was refluxed for half an hour. After cooling the solution to room temperature, the orange solid was filtered off. The yield (13) was 2.5 g (91%). Melting point 214°-216° C.

$^1$H-NMR (90 MHz, CDCl$_3$, TMS internal standard): δ=0.18 ppm (9H, s, Si(CH$_3$)$_3$), δ=1.40 ppm (9H, s, C(CH$_3$)$_3$), δ=1.99 ppm (1H, dd, J=14.5 Hz and J=3 Hz, H$_8$(ax)), δ=2.76 ppm (1H, d, J=14.5 Hz, H$_8$(eq)), δ=3.02 ppm (1H, d, J=19.5 Hz, H$_{10}$(ax)), δ=3.67 ppm (1H, d, J=19.5 Hz, H$_{10}$(eq)), δ=5.33 ppm (1H, m, H$_7$), δ=5.87 ppm (1H, s, OH), δ=7.72–7.87 ppm (2H, m, ArH), δ=8.25–8.39 ppm (2H, m, ArH), δ=13.33 ppm (1H, s, ArOH), δ=13.67 ppm (1H, s, ArOH).

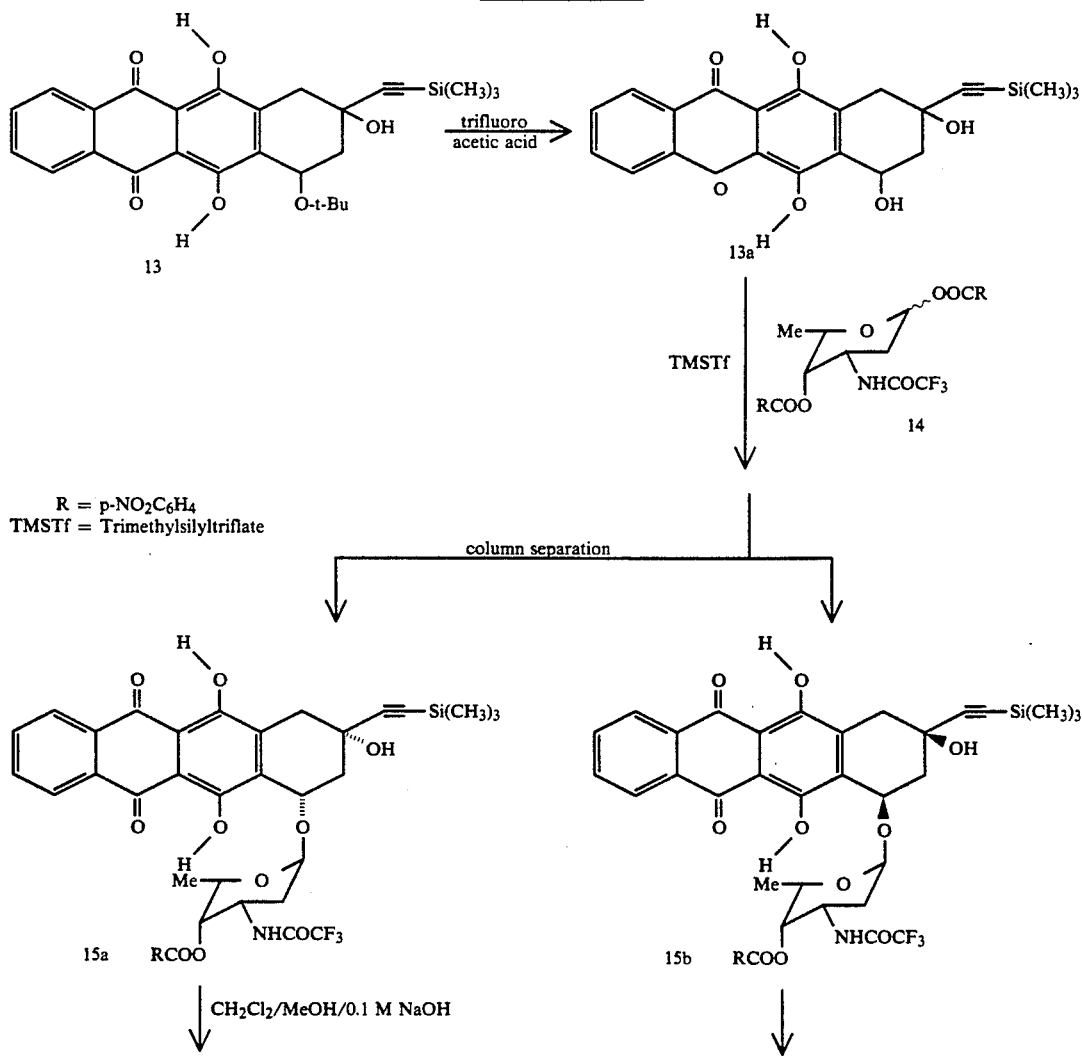

-continued
Reaction scheme B
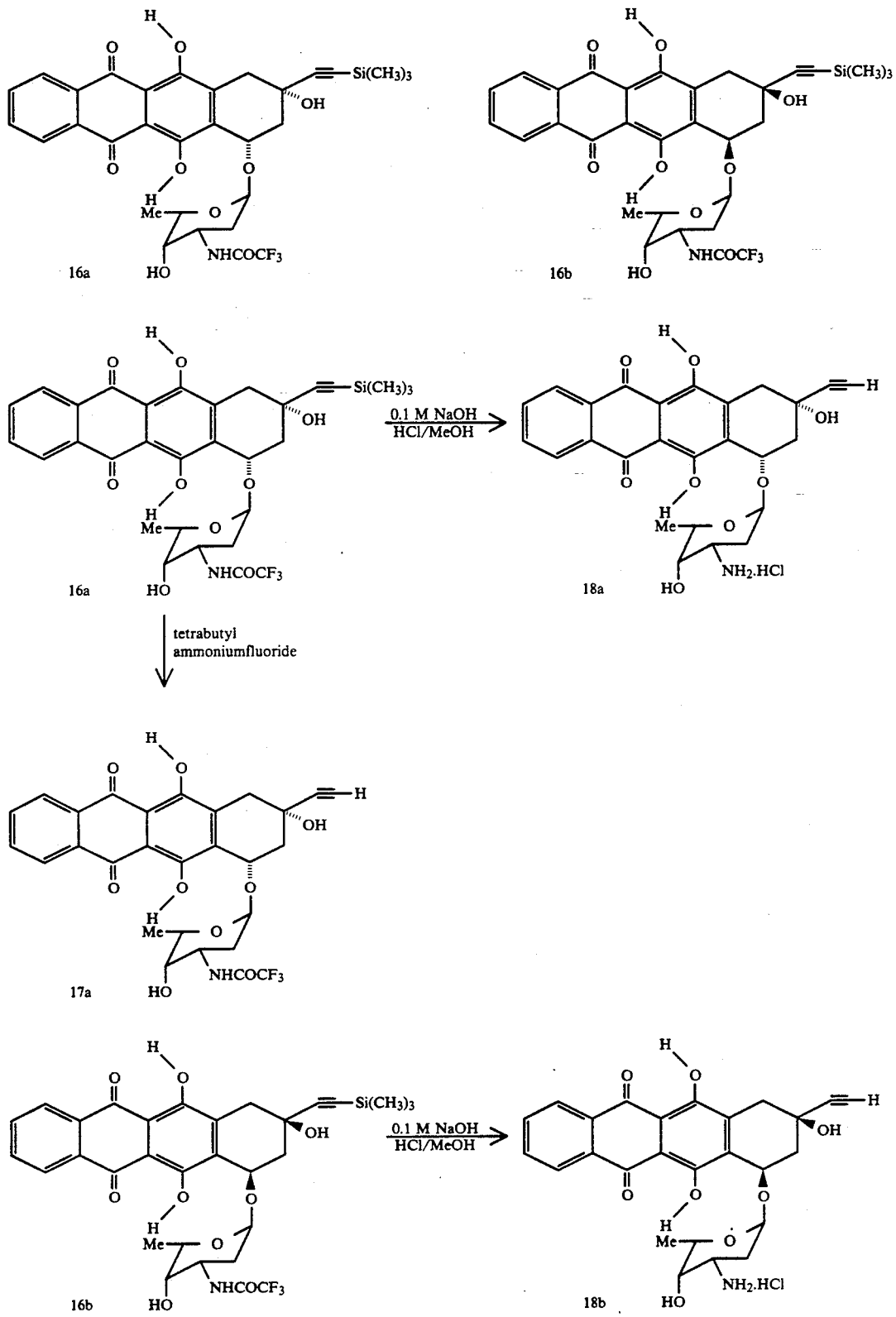

-continued
Reaction scheme B

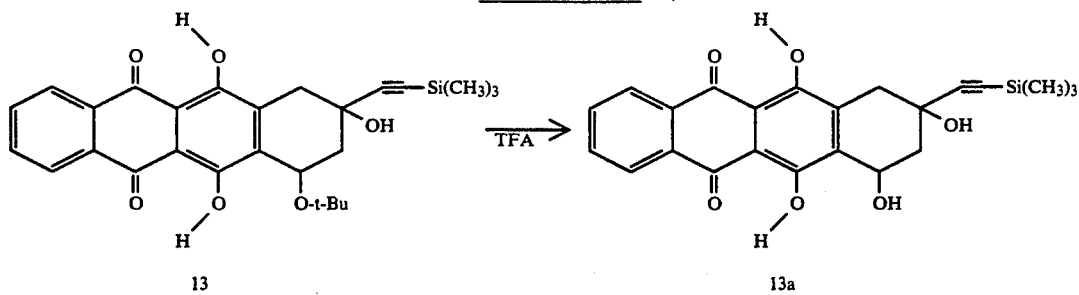

1.25 g (2.6 mmol) of (13) was dissolved in 15 ml of trifluoro acetic acid. The course of the reaction was followed by means of TLC (ethyl acetate:n-hexane, 3:5). After about 10 minutes the starting material had been reacted and the solution was poured into 200 ml of water and extracted with 3×75 ml of chloroform. After drying over anhydrous sodium sulphate and evaporating, compound 13a was purified via column chromatography (eluent ethyl acetate:n-hexane, 3:5). The yield (orange product, (13a)) was 0.89 g (81%). Melting point 208°-210° C.

$^1$H-NMR (400 MHz, CDCl$_3$, TMS internal standard): δ=0.20 ppm (9H, s, Si(CH$_3$)$_3$), δ=2.24 ppm (1H, dd, J=14.5 Hz and J=5.2 Hz, H$_8$(ax)), δ=2.65 ppm (1H, dt, J=14.5 Hz, J=2.3 Hz and J=2.2 Hz, H$_8$(eq)), δ=2.97 ppm (1H, d, J=18.8 Hz, H$_{10}$(ax)), δ=3.48 ppm (1H, dd, J=18.5 Hz and J=1.6 Hz, H$_{10}$(eq)), δ=3.49 ppm (1H, OH$_7$), δ=3.75 ppm (1H, br s, OH$_9$), δ=5.24 ppm (1H, br s, H$_7$), δ=7.82-8.32 ppm (4H, m, ArH), δ=13.27 ppm (1H, s, ArOH), δ=13.57 ppm (1H, s, ArOH).

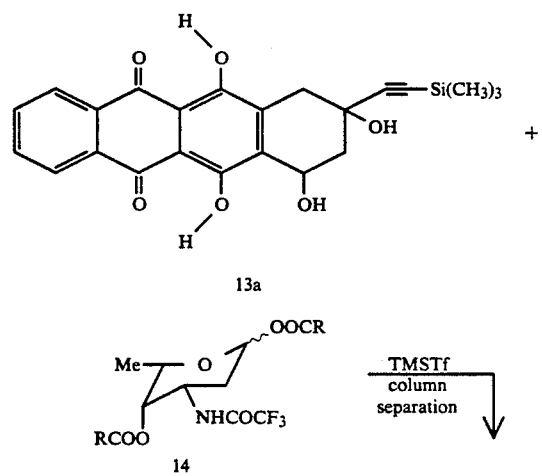

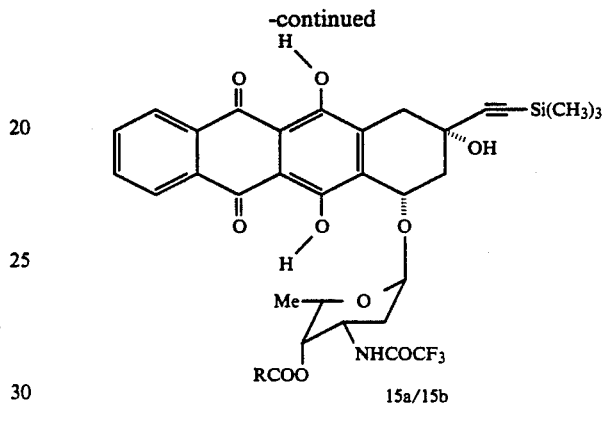

R = p-NO$_2$C$_6$H$_4$ 2.75 ml of Trimethylsilyl triflate (14.4 mmol) was added to a suspension of 3.55 g of 14 (6.6 mmol) and 20 g of 4 Å molecular sieve in a mixture of 125 ml of methylene chloride and 430 ml of diethylether (both distilled over CaH$_2$ and sodium, respectively) at −25° C. and under an argon atmosphere. The solution was stirred at 0° C. for one hour until to solution had become clear. Then the solution was cooled to −20° C. and 2.25 g (5.3 mmol) of 13a, dissolved in 250 ml of methylene chloride, was added. The reaction mixture was maintained at −20° C. during the addition and thereafter stirred at −20° C. during 3 hours. The course of the reaction was followed by means of TLC (eluent ethyl acetate:benzene, 1:4). After all of the starting material had been reacted, the reaction mixture was poured into a solution of 1000 ml of saturated sodium bicarbonate which was stirred vigorously. The organic layer was separated and thereafter washed with 1000 ml of water and 1000 ml of a saturated NaCl solution. After drying over sodium sulphate and evaporating, the compounds 15a and 15b were separated by means of column chromatography (eluent ethyl acetate:toluene, 1:16). After evaporation of the eluent and treatment with a small amount of n-hexane, 1.06 g (25%) of 15a could be isolated. Via a second column separation (eluent ethyl acetate:benzene, 1:6) 0.64 g (15%) of 15b could be isolated.

Compound 15a

Melting point 157°-159° C., [α$^{20}_D$]=−18.1° (c=0.105 in dioxan), $^1$H-NMR (400 MHz, CDCl$_3$, TMS internal standard): δ=0.20 ppm (9H, s, Si(CH$_3$)$_3$), δ=1.31 ppm (3H, d, J=6.5 Hz, 6'-Me), δ=2.03-2.19 ppm (2H, m, 2-H$_2$'), δ=2,33 ppm (1H, dd, J=14.5 Hz and J=4.8 Hz, H$_8$(ax)), δ=2.64 ppm (1H, br d, J=14.5 Hz, H$_8$(eq)), δ=3.02 ppm (1H, d, J=19 Hz, H$_{10}$(ax)), δ=3.57 ppm (1H, d, J=19 Hz, H$_{10}$(eq)), δ=3.76 ppm (1H, s, 9-OH), δ=4.48-4.58 ppm (2H, m, H₃', and H₅'), δ=5.17 ppm (1H, m, H₇), δ=5.44 ppm (1H, br s, H₄'), δ=5.68 ppm (1H, m, H₁'), δ=6.51 ppm (1H, br d, J=7.5 Hz, NH), δ=7.76-7.83 ppm (2H, m, ArH), δ=8.22-8.36 ppm (6H, m, ArH), δ=13.29 ppm (1H, s, ArOH), δ=13.59 ppm (1H, s, ArH).

Compound 15b

Melting point 160°-162° C., [α²⁰_D]=−310.7° (c=0.112 in dioxan), ¹H-NMR (400 MHz, CDCl₃, TMS internal standard): δ=0.22 ppm (9H, s, Si(CH₃)₃), δ=1.27 ppm (3H, d, J=6.5 Hz, 6'-Me), δ=1.92-2.18 ppm (3H, m, 2-H₂' and H₈(ax)), δ=2.90 ppm (1H, m, H₈(eq)), δ=3.10 ppm (1H, d, J=19 Hz, H₁₀(ax)), δ=3.70 ppm (1H, d, J=19 Hz, H₁₀(eq)), δ=4.21 ppm (1H, s, 9-OH), δ=4.59 ppm (1H, m, H₃'), δ=4.78 ppm (1H, q, J=6.5 Hz, H₅'), δ=5.44 ppm (1H, br s, H₇), δ=5.54 ppm (1H, m, H₄'), δ=5.58 ppm (1H, br d, J=3 Hz, H₁'), δ=6.36 ppm (1H, br d, J=7.5 Hz, NH), δ=7.85-7.89 ppm (2H, m, ArH), δ=8.25-8.41 ppm (6H, m, ArH), δ=13.35 ppm (1H, s, ArOH), δ=13.82 ppm (1H, s, ArH).

ylene chloride:acetone, 9:1). The yield was 0.31 g (76%).

Compound 16a

Melting point 140°-142° C., [α²⁰_D]=+237° (c=0.076 in dioxan), ¹H-NMR (400 MHz, CDCl₃, TMS internal standard): δ=0.20 ppm (9H, s, Si(CH₃)₃), δ=1.34 ppm (3H, d, J=6.5 Hz, 6'-Me), δ=1.79-2.03 ppm (2H, m, 2-H₂'), δ=2.01 ppm (1H, br s, 4'-OH), δ=2.28 ppm (1H, dd, J=14.7 Hz and J=4.5 Hz, H₈(ax)), δ=2.62 ppm (1H, m, H₈(eq)), δ=3.01 ppm (1H, d, J=19 Hz, H₁₀(ax)), δ=3.60 ppm (1H, dd, J=19 Hz and J=1.5 Hz, H₁₀(eq)), δ=3.64-3.69 ppm (1H, m, H₄'), δ=3.92 ppm (1H, s, 9-OH), δ=4.19-4.26 ppm (1H, m, H₃'), δ=4.32-4.38 ppm (1H, q, J=6.5 Hz, H₅'), δ=5.19 ppm (1H, dd, J=4 Hz and J=2 Hz, H₇), δ=5.53 ppm (1H, br d, J=4 Hz, H₁'), δ=6.65 ppm (1H, br d, J=8 Hz, NH), δ=7.82-7.86 ppm (2H, m, ArH), δ=8.33-8.38 ppm (2H, m, ArH), δ=13.35 ppm (1H, s, ArOH), δ=13.63 ppm (1H, s, ArH).

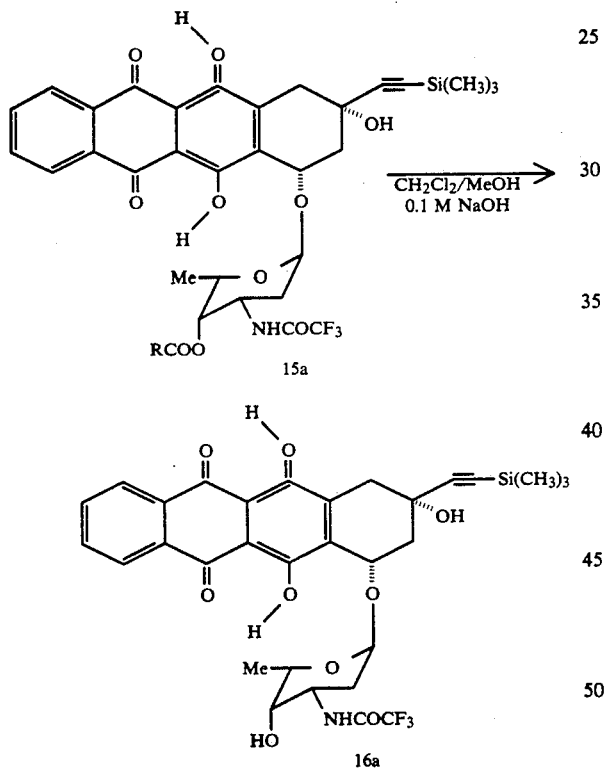

15a

16a

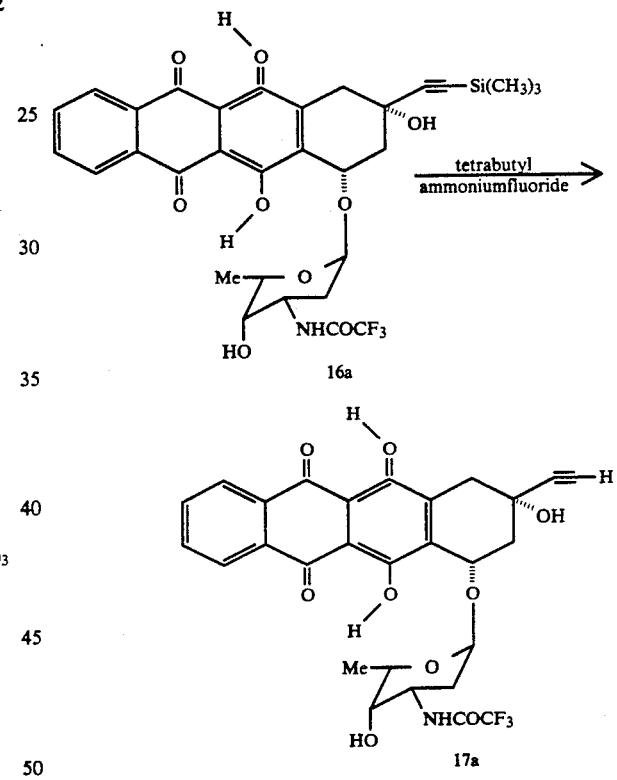

16a

17a 6.5 ml of a 0.1M NaOH solution was added to a stirred solution of 0.5 g (0.63 mmol) of 15a in 4 ml of methylene chloride and 260 ml of methanol at 0° C. and under an argon atmosphere. The deep purple solution was stirred at 0° C. for 5 minutes and the course of the reaction was followed by means of TLC (methylene chloride:acetone, 9:1). After the reaction some drops of glacial acetic acid were added until the solution became orange. Then 400 ml of ethyl acetate and 400 ml of a saturated NaCl solution were added to the solution. The organic layer was twice extracted with 130 ml of a saturated NaCl solution and dried over sodium sulphate. After evaporating the orange residue was purified by means of column chromatography (eluent meth- 0.244 g of compound 16a was dissolved in 25 ml of THF. 0.178 g of tetrabutylammoniumfluoride was added. The reaction mixture was stirred for 5 minutes. Then 100 ml of water and 100 ml of chloroform were added. The water layer was twice extracted with 100 ml of chloroform. The organic fraction was dried over anhydrous sodium sulphate and evaporated. After column separation (methylene chloride:acetone, 7:3) 0.13 g of compound 17a could be isolated (60%).

Compound 17a

Melting point 146°-148° C., [α²⁰_D]=289° C. (c=0.076 in dioxan0, ¹H-NMR (400 MHz, CDCl₃, TMS internal standard): δ=1.31 ppm (3H, d, J=6.5 Hz, 6'-Me), δ=1.80-2.08 ppm (3H, m, 2-H₂' and H₈(ax)), δ=2.18 ppm (1H, br s, 4'-OH), δ=2.57 ppm (1H, s, C≡C—H), δ=2.87 ppm (1H, m, H₈(eq)), δ=3.10 ppm (1H, d, J=19 Hz, H₁₀(ax)), δ=3.71 ppm (1H, d, J=19

Hz, $H_{10}(eq)$), δ=3.62 ppm (1H, m, $H_{4'}$), δ=4.30 ppm (1H, s, 9-OH), δ=4.31 ppm (1H, m, $H_{3'}$), δ=4.59 ppm (1H, m, $H_{5'}$), δ=5.41 ppm (1H, m, $H_7$), δ=5.51 ppm (1H, br s, $H_{1'}$), δ=6.64 ppm (1H, br d, J=8 Hz, NH), δ=7.83–7.88 ppm (2H, m, ArH), δ=8.35–8.40 ppm (2H, m, ArH), δ=13.41 ppm (1H, s, ArOH), δ=13.79 ppm (1H, S, ArH).

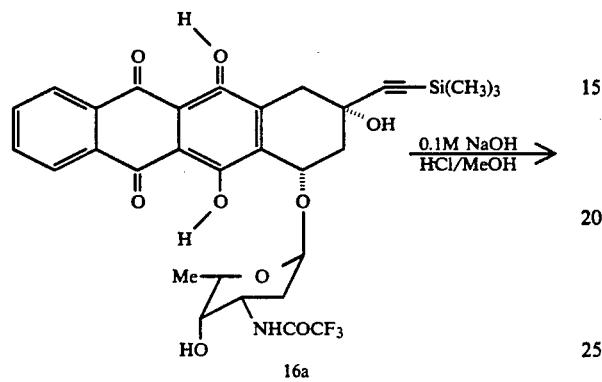

16a

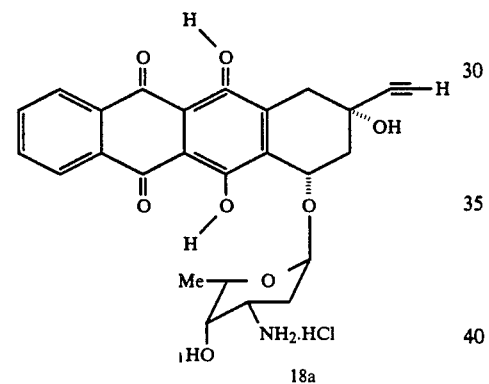

18a 0.15 g (0.23 mmol) of compound 16a was dissolved in 3 ml of acetone. 30 ml of 0.1M NaOH was added and reaction mixture was stirred at room temperature and under an argon atmosphere for 30 minutes. The reaction was followed by means of TLC (water:acetic acid:methanol:chloroform, 12:26:54:160). Then the solution was acidified with 1M HCl to pH 9. The neutralized solution was extracted several times with 75 ml of chloroform until the organic layer did not colour anymore. The combined organic layers were washed with water and dried over sodium sulphate. After filtration and evaporation, the residue was dissolved in a minimum amount of a solution of chloroform and methanol (9/1). After the addition of 0.4 ml of 0.6M HCl in methanol and 50 ml of diethylether the HCl salt precipitated. After filtration, 0.084 g (70%) of compound 18a could be isolated.

Compound 18a

Melting point 177°–179° C., $[\alpha^{20}_D]=189°$ (c=0.037 in dioxan).

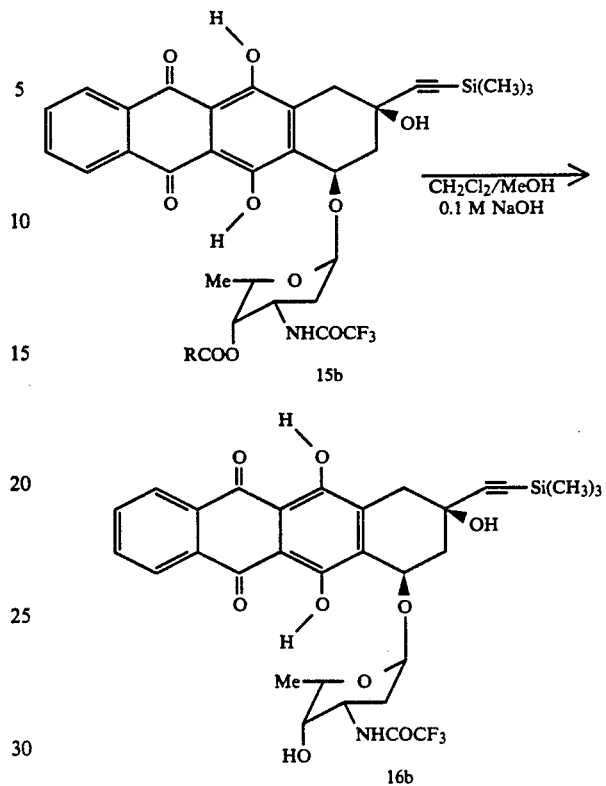

15b

16b 11.8 ml of a 0.1M NaOH solution was added to a stirred solution of 0.9 g (1.13 mmol) of 15b in 7 ml of methylene chloride en 475 ml of methanol at 0° C. and under an argon atmosphere. The deep purple solution was stirred at 0° C. for 20 minutes and the course of the reaction was followed by means of TLC (methylenen chloride:acetone, 9:1). After the reaction a few drops of glacial acetic acid were added until the solution became orange. Then 750 ml of ethyl acetate and 750 ml of a saturated NaCl solution were added to the solution. The oganic layer was twice extracted with 190 ml of a saturated NaCl solution and dried over sodium sulphate. After evaporating the orange residue was purified by means of column chromatography (eluent methylene chloride:acetone, 9:1). The yield was 0.58 g (80%).

Compound 16b

Melting point 138°–140° C., $[\alpha^{20}_D]=-375°$ (c=0.0885 in dioxan).

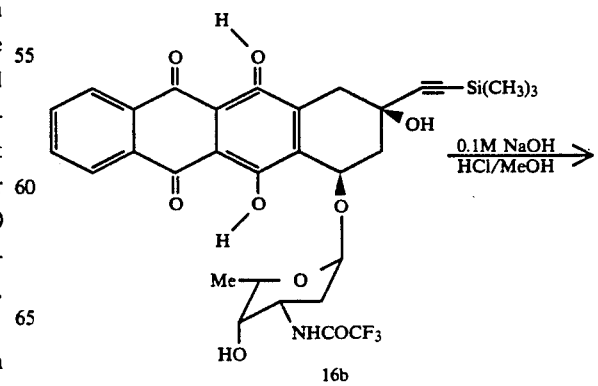

16b

21

-continued

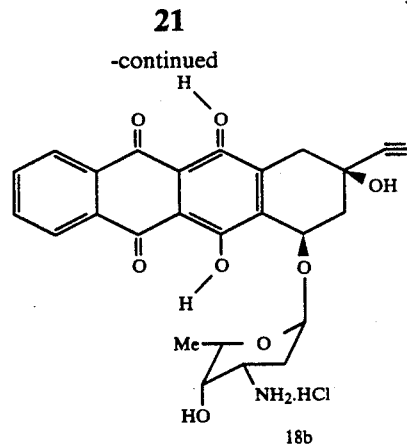

18b 0.250 g (0.39 mmol) of compound 16b was dissolved in 5 ml of acetone. 50 ml 0.1M NaOH was added thereto and the reaction mixture was stirred at room temperature and under an argon atmosphere for 30 minutes. The reaction was followed by means of TLC (water:acetic acid:methanol:chloroform, 12:26:54:160). After the reaction the solution was acidified with 1M HCl to pH 9. The neutralized solution was extracted several times with 100 ml of chloroform until the organic layer no longer coloured. The combined organic layers were washed with water and dried over sodium sulphate. After filtration and evaporation the residue was dissolved in a minimum amount of a solution of chloroform and methanol (9/1). After the addition of 0.7 ml of 0.6M HCl in methanol and 100 ml of diethylether the NCl salt precipitated. After filtrating, 0.140 g (70%) of compound 18b could be isolated.

Compound 18b

Melting point 160°–162° C., $[\alpha^{20}_D] = -280°$ (c=0.0275 in dioxan).

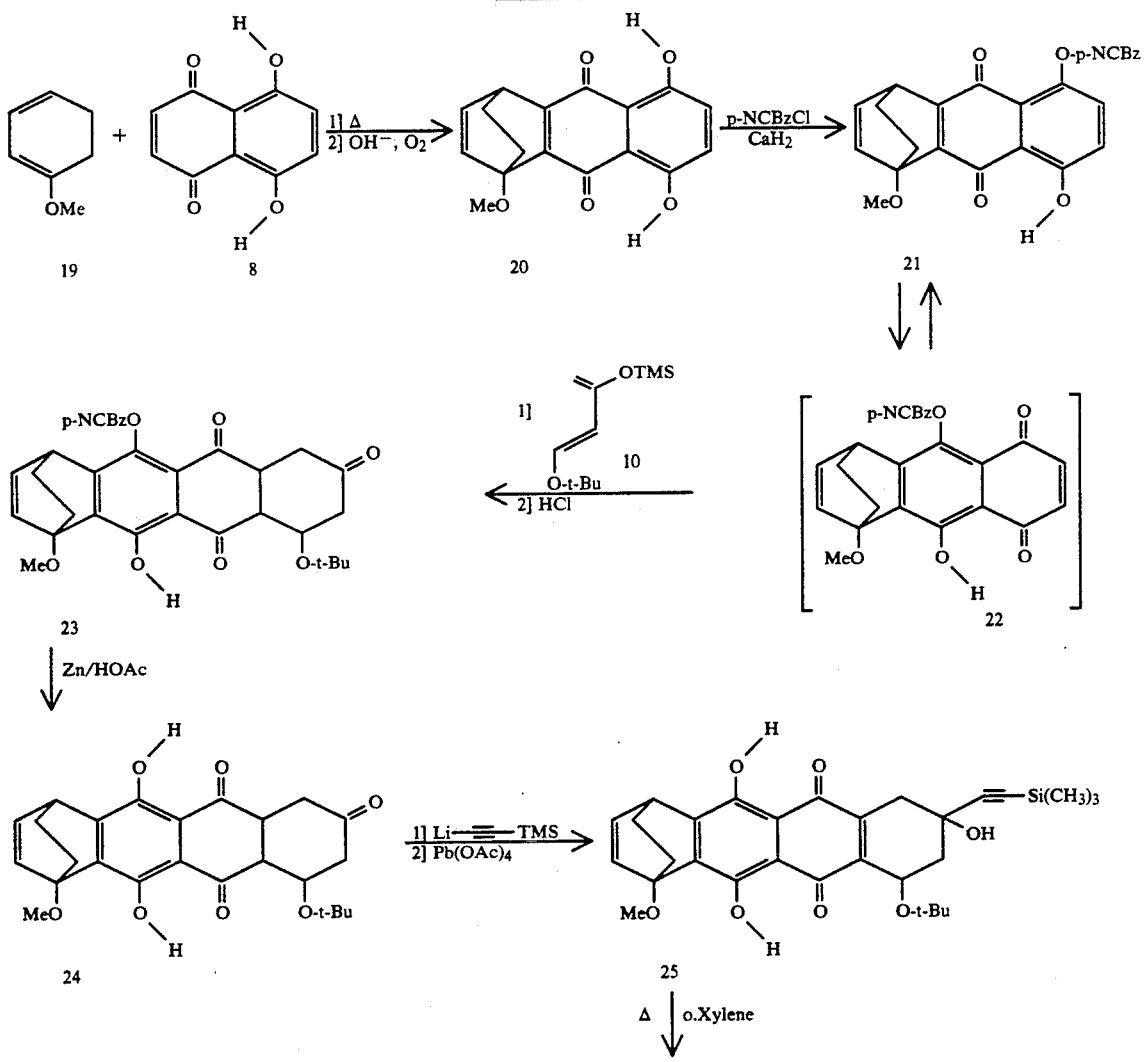

-continued
Reaction scheme C

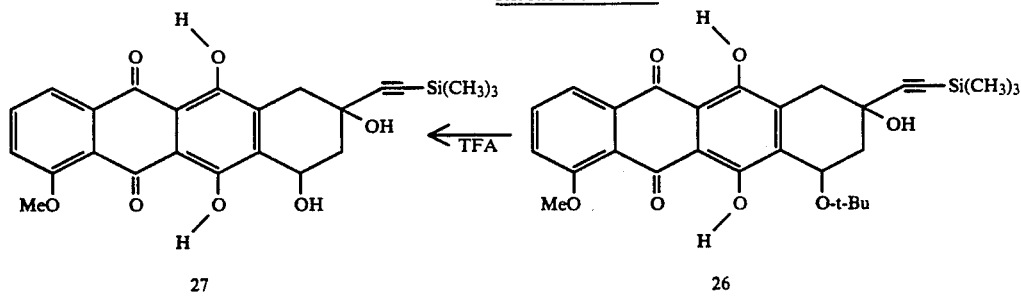

1,4,9,10-tetrahydro-5,8-dihydroxy-1-methoxy-9,10-dioxo-1,4-ethanoanthracene (20)

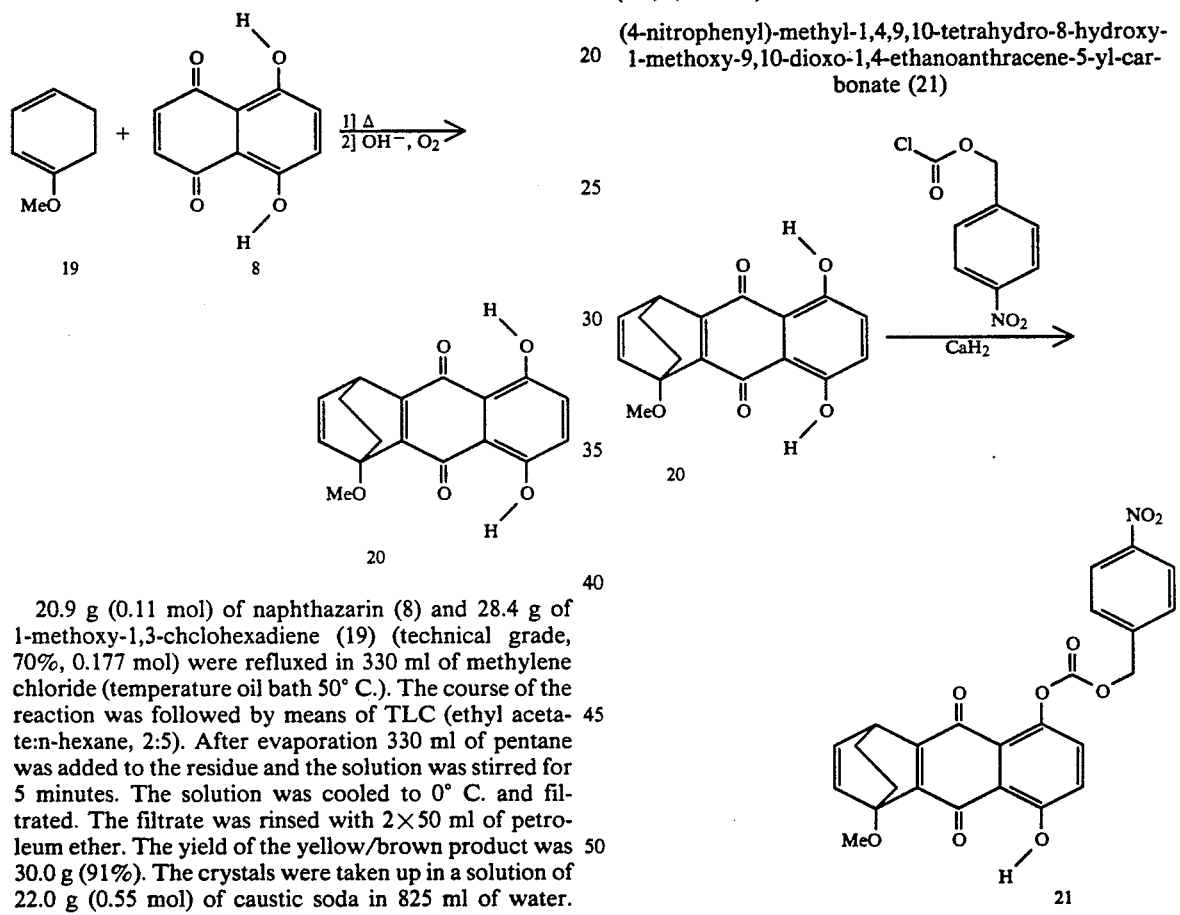

20.9 g (0.11 mol) of naphthazarin (8) and 28.4 g of 1-methoxy-1,3-chclohexadiene (19) (technical grade, 70%, 0.177 mol) were refluxed in 330 ml of methylene chloride (temperature oil bath 50° C.). The course of the reaction was followed by means of TLC (ethyl acetate:n-hexane, 2:5). After evaporation 330 ml of pentane was added to the residue and the solution was stirred for 5 minutes. The solution was cooled to 0° C. and filtrated. The filtrate was rinsed with 2×50 ml of petroleum ether. The yield of the yellow/brown product was 30.0 g (91%). The crystals were taken up in a solution of 22.0 g (0.55 mol) of caustic soda in 825 ml of water. During half an hour air was passed through the solution while the solution was stirred. The colour of the solution changed from green to blue. The course of the reaction was followed by means of TLC (ethyl acetate:n-hexane, 2:5). After the reaction 46.2 ml of concentrated HCl (37%) was added to the solution. The product precipitated as a red solid which was filtered off. This compound was dried on a film evaporator (2 mm Hg) and in a vacuum dessicator (over $P_2O_5$) during at least one night. The yield of the red compound (20) was 27.0 g (91%). The overall yield was 83%. Melting point 239°-241° C. $^1$H-NMR (90 MHz, CDCl$_3$, TMS internal standard): $\delta=1.39$-1.92 ppm (4H, m, CH$_2$—CH$_2$), $\delta=3,69$ ppm (3H, s, OMe), $\delta=4,53$ ppm (1H, m, H$_4$), $\delta=6.40$ ppm (1H, dd, J=5.6 Hz and J=8 Hz), $\delta=6.64$ ppm (1H, dd, J=8 Hz and J=1.5 Hz), $\delta=7.12$ ppm (2H, s, ArH), $\delta=12.60$ ppm (1H, s, ArOH), $\delta=13.06$ ppm (1H, s, ArOH).

(4-nitrophenyl)-methyl-1,4,9,10-tetrahydro-8-hydroxy-1-methoxy-9,10-dioxo-1,4-ethanoanthracene-5-yl-carbonate (21)

12.0 g (0.04 mol) of (20) was dissolved in 300 ml of THF which had been distilled over sodium. 12.6 g (0.058 mol) of para-nitrobenzyloxycarbonyl chloride and 1.7 g (0.04 mol) of calcium hydride were added thereto. The solution was caused to vibrate by means of a direct immersion sonic horn at 0° C. for 6 hours. Then the solution was caused to vibrate in an ultrasonic cleaning bath during 24 hours. The colour of the solution changed from red to yellow. The course of the reaction was followed by means of TLC (ethyl acetate:n-hexane, 2:5). Then the reaction mixture was poured into 500 ml of a 5% NaH$_2$PO$_4$ solution and extracted with 2×500 ml of chloroform. The organic phase was dried over anhydrous sodium sulphate and evaporated. The crude reaction mixture was purified by means of column chromatography (eluent ethyl acetate:toluene:n-hexane, 1:5:5) and after evaporation stirred into 200 ml of diethylether. The first yellow fraction was the desired product (9.6 g, 50%). Melting point 136°–137° C.

¹H-NMR (90 MHz, CDCl₃, TMS internal standard): δ=1.33–1.89 ppm (4H, m, CH₂—CH₂) δ=3.66 ppm (3H, s, OMe), δ=4.30–4.47 ppm (1H, m, H₄), δ=5.44 ppm (2H, s, CH₂), δ=6.34 ppm (1H, dd, J=5.6 Hz and J=8 Hz, H₃), δ=6.61 ppm (1H, dd, J=8 Hz and J=1.5 Hz, H₂), δ=7.26 ppm (2H, s, ArH), δ=7.54 ppm (2H, AB, J=8,5 Hz, ArH), δ=8.26 ppm (2H, AB, J=8.75 Hz, ArH), δ=12.72 ppm (1H, s, ArOH).

1,4,6a,9,10,10a-hexahydro-12-hydroxy-10-tert-butoxy-1-methoxy-6,8,11-(7H)-trioxo-1,4-ethanonaphthacene-5-yl-(4-nitrophenyl)-methylcarbonate (23)

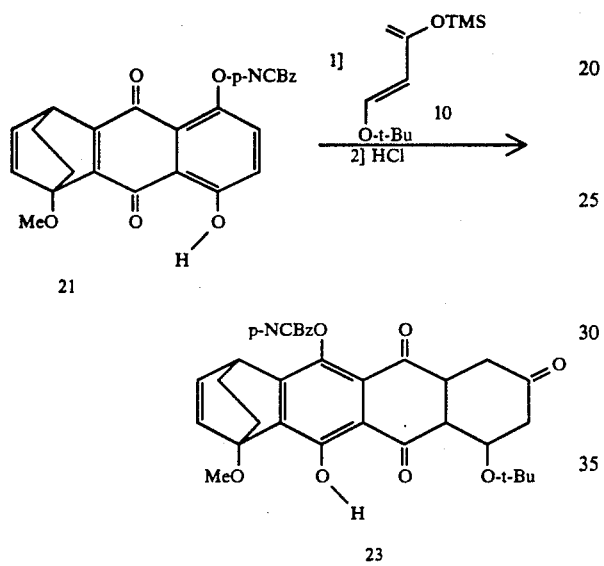

7.5 g (0.0157 mol) of (21) was dissolved in 175 ml of THF which has been distilled over Na. Then an argon atmosphere was applied and 6.75 g (0.0315 mol) of 1-tert-butoxy-3-trimethylsilyloxybuta-1,3-diene (10) was added. The mixture was stirred at room temperature for two days. The course of the reaction was followed by means of TLC (ethyl acetate:n-hexane, 2:5). The colour of the reaction mixture changed from yellow/-orange to yellow/green. After the reaction the solution was evaporated and the residue was dissolved in 150 ml of cold THF (0° C.). 8.75 ml of 1M HCl was added to the solution and the solution was stirred at 0° C. for 15 minutes. The course of the reaction was followed by means of TLC (ethyl acetate:n-hexane, 3:5). After the reaction 175 ml of water was added and the aqueous solution was extracted with 2×125 ml of methylene chloride. The collected organic fractions were dried over sodium sulphate and evaporated. The residue was stirred in 300 ml diethylether for one night. After cooling to 0° C. the yellow crystals were filtered off (7.8 g, 80%). Melting point 147°–150° C.

¹H-NMR (90 MHz, CDCl₃, TMS internal standard): (Mixture of endo and exo isomers) δ=0.74 ppm (9H, s, C(CH₃)₃), δ=1.43–1.93 ppm (4H, m, CH₂—CH₂), δ=2.08–2.62 ppm (3H, H₇(ax), H₉(eq) and H₉(ax)), δ=3.23–3.70 ppm (3H, H₁₀ₐ, H₆ₐ and H₇(eq)), δ=3,74 ppm (3H, s, OMe), δ=4.11–4.26 ppm (1H, m, H₁₀), δ=4.43–4.56 ppm (1H, H₄), δ=5,42 ppm (2H, CH₂), δ=6.26–6.80 ppm (2H, H—C=C—H), δ=7.56–8.33 ppm (4H, ArH), δ=13.19 ppm (1H, s, ArOH).

1,4,6a,10,10a-hexahydro-5,12-dihydroxy-10-tert-butoxy-1-methoxy-1,4-ethanonaphthacene-6,8,11-(7H)-trione (24)

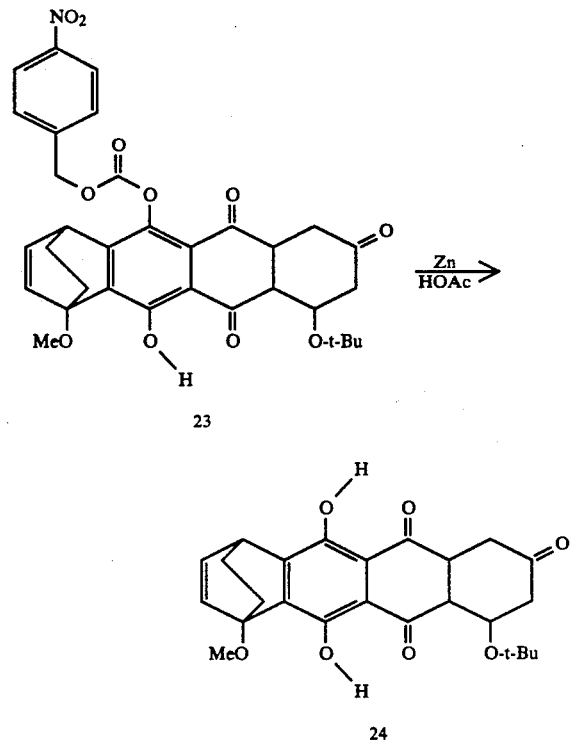

5.0 g (0.0081 mol) of (23) was dissolved in 20 ml of THF. After the solution had been cooled to 0° C., 20 ml of glacial acetic acid and 5.2 g (0.08 mol) of zinc were added. The reaction mixture was stirred at 0° C. for 15 minutes. The course of the reaction was followed by means of TLC (ethyl acetate: n-hexane, 3:5). After 15 minutes 5.2 g of Zn was added again. After the reaction the reaction mixture was poured into 150 ml of methylene chloride. Then the acetic acid was neutralized with a saturated sodium bicarbonate solution until the pH of the water layer had increased to 6. The layers were separated and the water layer was extracted with 2×150 ml of methylene chloride. The collected organic fractions were washed with a saturated NaCl solution (250 ml). After drying (anhydrous sodium sulphate) the solution was evaporated and the residue was stirred in 500 ml of diethylether for one night. After cooling to 0° C. the light yellow crystals (3.45 g, 97%) were filtered off. Melting point 134°–136° C.

¹H-NMR (90 MHz, CDCl₃, TMS internal standard): (Mixture of endo and exo isomers) δ=0.71 ppm (9H, s, C(CH₃)₃), δ=1.38–1.89 ppm (4H, m, CH₂—CH₂), δ=2.22–2.64 ppm (3H, H₇(ax)+H₉(eq)+H₉(ax)), δ=3.33–3.75 ppm (3H, H₁₀ₐ+H₆ₐ+H₇(eq)), δ=3.69 ppm (3H, OMe), δ=4.34–4.62 ppm (2H, H₄+H₁₀), δ=6.04–6.75 ppm (2H, H—C=C—H), δ=11.86 ppm (1H, ArOH), δ=12.92 ppm (1H, ArOH).

cis-8-trimethylsilylethynyl-7,8,9,10-tetrahydro-6,8,11-trihydroxy-10-tert-butoxy-1-methoxy-naphthacene-5,12-dione (26).

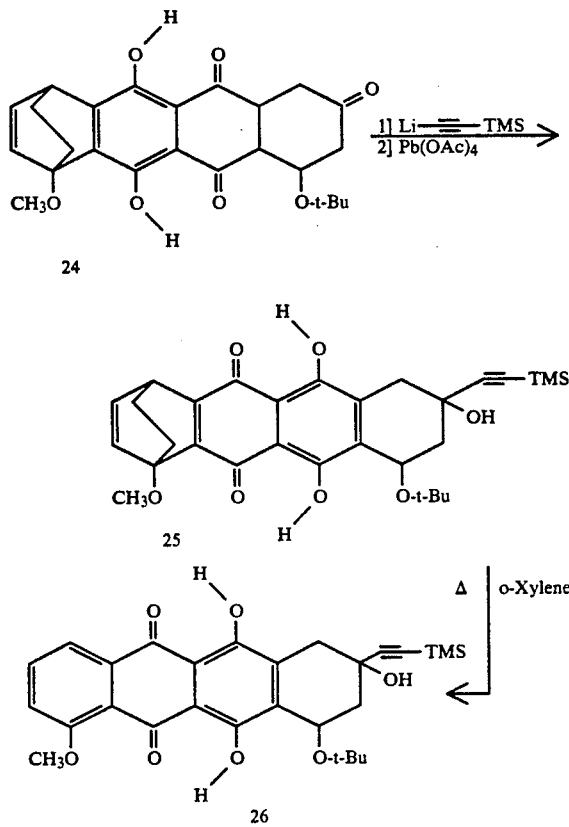

5.7 g (0.058 mol) of trimethylsilyl acetylene was dissolved in 750 ml THF, which had been distilled over sodium, and an argon atmosphere was applied. Then the solution was cooled to −78° C. and 37,9 ml of 1.5M BuLi (0.057 mol) was added dropwise. The reaction mixture was stirred at −78° C. for 30 minutes. 5.0 g (0.0114 mol of (24) was added to the reaction mixture. The course of the reaction was followed by means of TLC (ethyl acetate:n-hexane, 2:5). The colour of the solution changed from green to green/yellow. After about 2 hours the reaction mixture was allowed to come slowly to room temperature and 250 ml of a 10% $NH_4Cl$ solution was added. After stirring for 15 minutes the solution was diluted with 500 ml of water and extracted with 2×500 ml of chloroform. The collected organic fractions were evaporated and the residue was dissolved in 100 ml of glacial acetic acid. To the solution 5.5 g (0.012 mol) of lead tetraacetate was added and the solution was stirred at room temperature for one night. The course of the reaction was followed by means of TLC (ethyl acetate:n-hexane, 2:5). The colour of the solution changed from yellow/red to red. After the reaction the reaction mixture was poured into 400 ml of water. The red solid was filtered off and the filtrate was dissolved in chloroform. The organic fraction was washed with a saturated sodium bicarbonate solution and dried over anhydrous sodium sulphate. The crude reaction mixture was dissolved in 50 ml of o-xylene. The solution was refluxed for 3 hours (temperature oil bath 150° C.). The course of the reaction was followed by means of TLC (ethyl acetate:n-hexane, 3:5) and the colour of the solution changed from red to orange. After the reaction the solution was evaporated and the product recrystallized in diethylether. The yield (orange crystals) was 4.2 g (73%). Melting point 247°–250° C.

$^1$H-NMR (90 MHz, $CDCl_3$, TMS internal standard): δ=0.23 ppm (9H, s, $Si(CH_3)_3$), δ=1.39 ppm (9H, s, $C(CH_3)_3$), δ=1.99 ppm (1H, dd, J=15 Hz, J=3 Hz, $H_9(ax)$), δ=2.72 ppm (1H, d, J=15 Hz, $H_9(eq)$), δ=2.98 ppm (1H, d, J=20 Hz, $H_7(ax)$), δ=3.64 ppm (1H, d, J=20 Hz, $H_7(eq)$), δ=4.05 ppm (3H, s, $OCH_3$), δ=5.35 ppm (1H, m, $H_{10}$), δ=5.87 ppm (1H, s, OH), δ=7.23–8.05 ppm (3H, m, ArH), δ=12.99 ppm (1H, s, ArOH), δ=13.8 ppm (1H, s, ArOH).

cis-8-trimethylsilylethynyl-7,8,9,10-tetrahydro-6,8,10,11-tetrahydroxyl-methoxynaphthacene-5,12-dione (27).

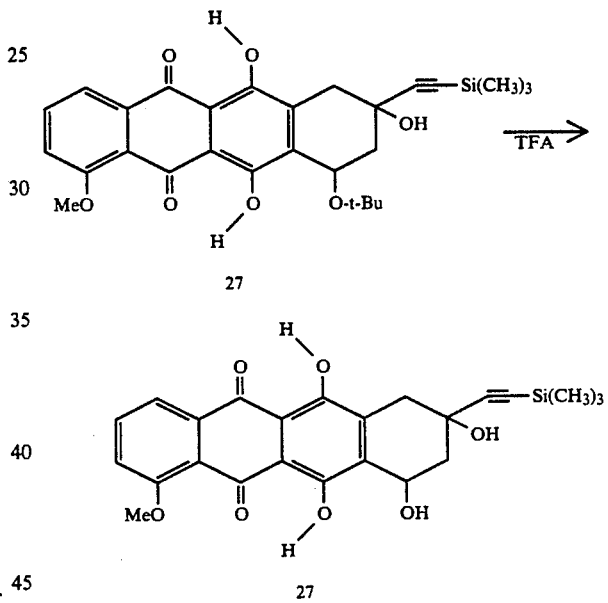

0.81 g (1.59 mmol) of (26) was dissolved in 15 ml of trifluoro acetic acid. The course of the reaction was followed by means of TLC (ethyl acetata:n-hexane, 3:5). After about 10 minutes the starting material was converted and the reaction mixture was poured into 250 ml of water and extracted with $CHCl_3$ until the water layer was colourless. Compound 27 was purified by means of column chromatography (eluent 3% methanol in chloroform). The yield (orange product) was 0.55 g (76%). Melting point 235°–237° C.

$^1$H-NMR (400 MHz, $CDCl_3$, TMS internal standard): δ=0.19 ppm (9H, s, $Si(CH_3)_3$), δ=2.26 ppm (1H, dd, J=14.5 HZ and J=5 Hz, $H_9(ax)$), δ=2.76 ppm (1H, dt, J=14.5 Hz, J=2.0 Hz and J=2.5 Hz, $H_9(eq)$), δ=2.96 ppm (1H, d, J=18.6 Hz, $H_7(ax)$), δ=3.48 ppm (1H, d, J=18.6 Hz and J=2.0 Hz, $H_7(eq)$), δ=3.54 (1H, s, 10-OH), δ=3.68 ppm (1H, d, J=4.0 Hz, 7-OH), δ=4.09 (3H, s, $OCH_3$), δ=5.28 ppm (1H, m, $H_7$), δ=7.38–8.05 ppm (3H, ArH), δ=13.29 ppm (1H, s, ArOH), δ=14.03 ppm (1H, s, ArOH).

Reaction scheme D
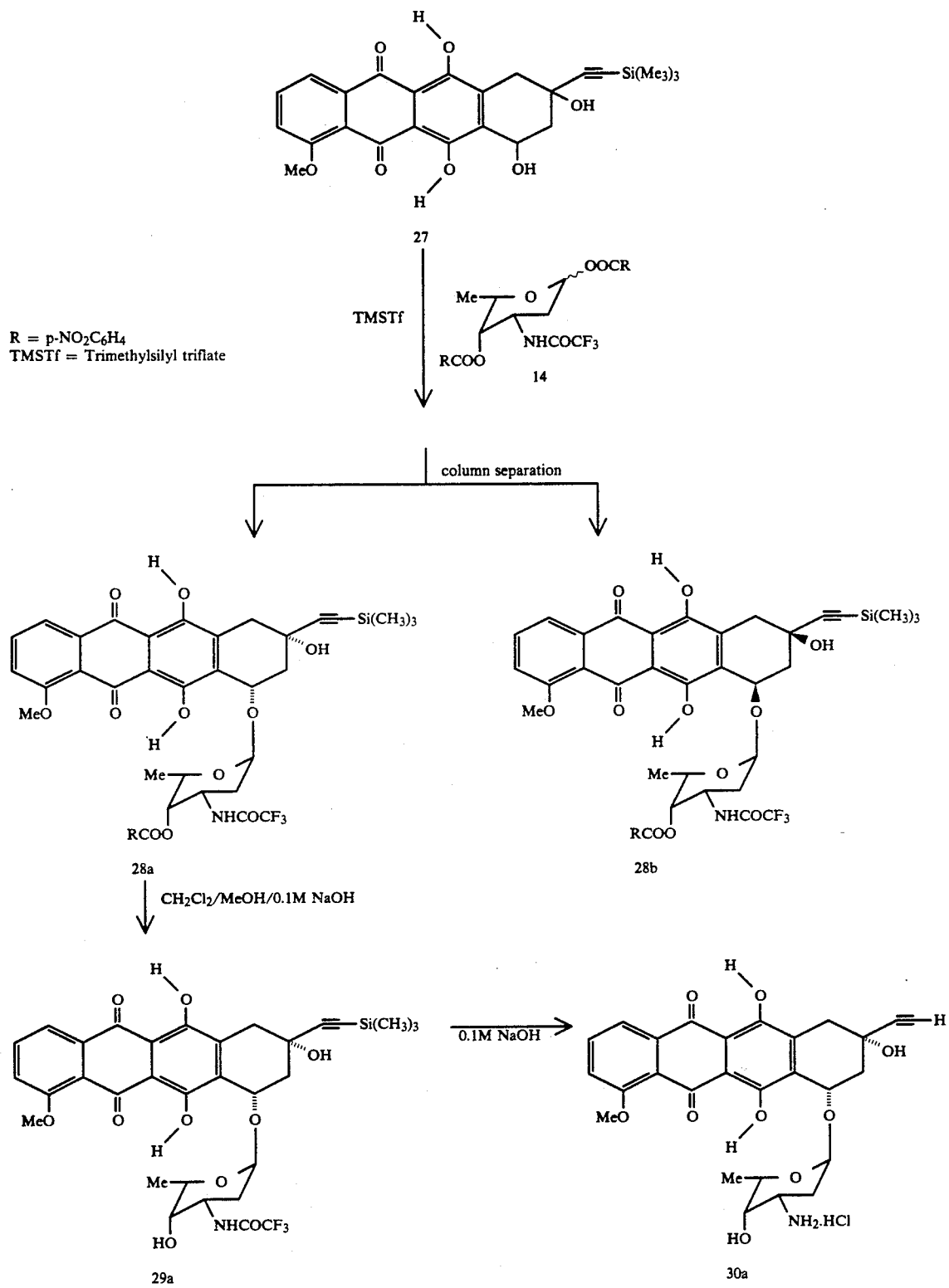

-continued
Reaction scheme D

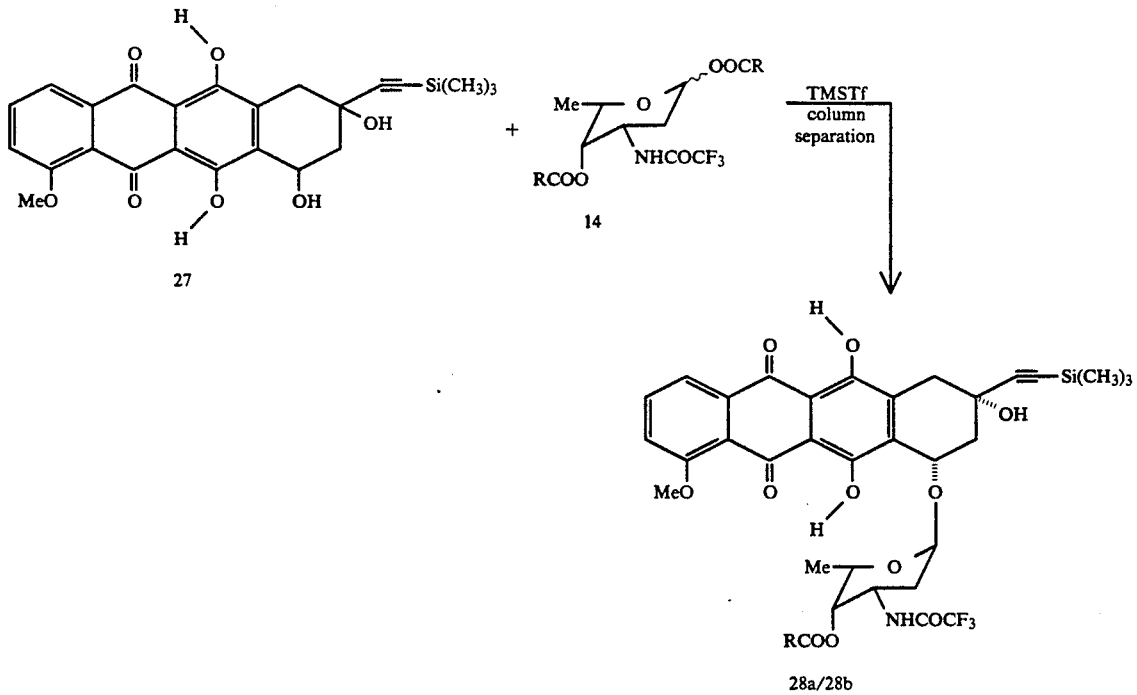

27

14

28a/28b 1.0 ml of trimethylsilyl triflate was added to a suspension of 1.22 g of 14 (2.26 mmol) and 16 g of 4 Å molecular sieve in a mixture of 150 ml of methylene chloride and 50 ml of diethyl ether (both distilled over $CaH_2$ and sodium, respectively) at $-25°$ C. and under an argon atmosphere. The solution was stirred at 0° C. for 1 hour until the solution had become clear. Then the solution was cooled to $-25°$ C. and 0.8 (1.8 mmol) of 27, dissolved in 200 ml of methylene chloride, was added. The reaction mixture was maintained at $-20°$ C. during the addition and then stirred at $-20°$ C. for 3 hours. The course of the reaction was followed by means of TLC (eluent ethyl acetate:benzene, 1:4). After all the starting material had been converted, the reaction mixture was poured into a solution of 800 ml of saturated sodium bicarbonate which was vigorously stirred. The organic layer was separated and then washed with 500 ml of water and 500 ml of a saturated NaCl solution. After drying over sodium sulphate and evaporation, the compounds 28a and 28b were separated by means of column chromatography (eluent 2% of acetone and 0.2% of glacial acetic acid in methylene chloride). After evaporation of the eluent and treatment with a small amount of n-hexane, 0.12 g (8%) of 28a and 0.17 g (12%) of 28b could be isolated.

Compound 28a

Melting point 161°–163° C., $[\alpha^{20}_D] = +6°$ (c=0.5 in dioxan), $^1$H-NMR (400 MHz, CDCl$_3$, TMS internal standard): $\delta=0.20$ ppm (9H, s, Si(CH$_3$)$_3$), $\delta=1.29$ ppm (3H, d, J=6.5 Hz, 6'-Me), $\delta=2.04$ ppm (2H, dd, J=9 Hz and J=2.3 Hz, 2-H$_2$'), $\delta=2.33$ ppm (1H, dd, J=14.7 Hz and J=4.9 Hz, H$_9$(ax)), $\delta=2.61$ ppm (1H, m, H$_9$(eq)), $\delta=3.01$ ppm (1H, d, J=18,7 Hz, H$_7$(ax)), $\delta=3.57$ ppm (1H, dd, J=18.7 Hz and J=1.2 Hz, H$_7$(eq)), $\delta=3.70$ ppm (1H, s, 8-OH), $\delta=4.07$ ppm (3H, s, OMe), $\delta=4.44$–4.55 ppm (2H, m, H$_3$' and H$_5$'), $\delta=5.23$ ppm (1H, br s, H$_{10}$), $\delta=5.46$ ppm (1H, m, H$_4$'), $\delta=5.71$ ppm (1H, br s, H$_1$'), $\delta=6.22$ ppm (1H, br d, J=7.5 Hz, NH), $\delta=7.37$–8.04 ppm (3H, m, ArH), $\delta=8.27$–8.36 ppm (4H, m, ArH), $\delta=13.29$ ppm (1H, s, ArOH), $\delta=14.07$ ppm (1H, s, ArH).

Compound 28b

Melting point 174°–176° C., $[\alpha^{20}_D] = -347.7°$ (c=0.65 in dioxan), $^1$H-NMR (400 MHz, CDCl$_3$, TMS internal standard): $\delta=0.22$ ppm (9H, s, Si(CH$_3$)$_3$), $\delta=1.25$ ppm (3H, d, J=6.5 Hz, 6'-Me), $\delta=1.90$–2.17 ppm (3H, m, 2-H$_2$' and H$_9$(ax)), $\delta=2.86$–2.92 ppm (1H, m, H$_9$(eg)), $\delta=3.08$ (1H, d, J=19 Hz, H$_7$(ax)), $\delta=3.71$ ppm (1H, dd, J=19 Hz and J=1.3 Hz, H$_7$(eq)), $\delta=4.11$ ppm (3H, s, OMe), $\delta=4.23$ ppm (1H, s, 8-OH), $\delta=4.52$–4.57 ppm (1H, m, H$_3$'), 4.76–4.84 ppm (1H, m, H$_5$'), $\delta=5.40$ ppm (1H, br s, H$_{10}$), $\delta=5.56$ ppm (1H, br s, H$_4$'), $\delta=5.57$ ppm (1H, br s, H$_1$'), $\delta=6.27$ ppm (1H, br d, J=7.5 Hz, NH), $\delta=7.79$–8.27 ppm (3H, m, ArH), $\delta=8.28$–8.35 ppm (4H, m, ArH), $\delta=13.31$ ppm (1H, s, ArOH), $\delta=14.23$ ppm (1H, s, ArH).

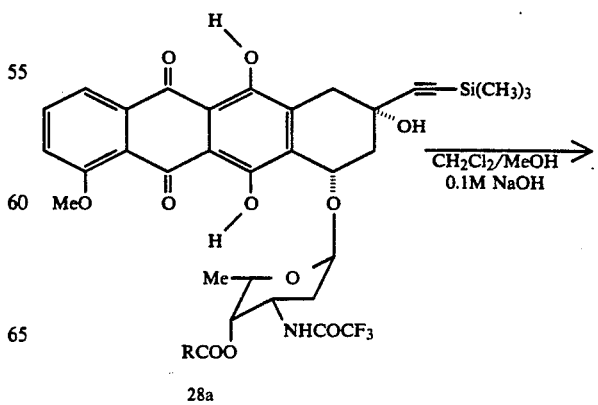

28a

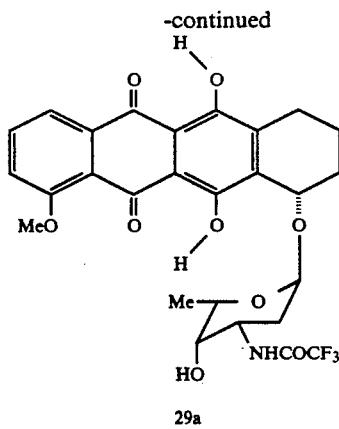

29a

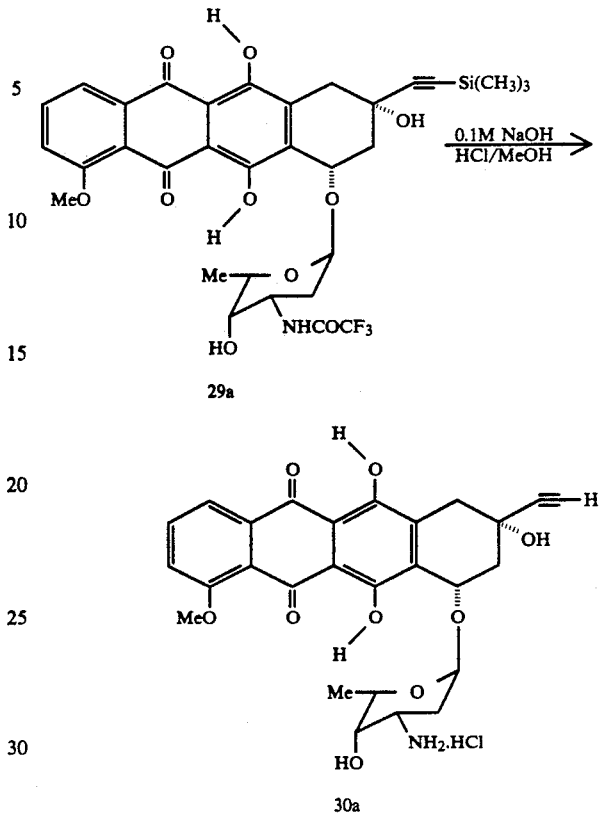

29a

30a 1.2 ml of a 0.1M NaOH solution was added to a stirred solution of 0.09 g (0.11 mmol) of 28a in 0.75 ml of methylene chloride and 37 ml of methanol at 0° C. and under an argon atmosphere. The deep purple solution was stirred at 0° C. for 3 minutes and the course of the reaction was followed by means of TLC (methylene chloride:acetone, 9:1). After the reaction a few drops of glacial acetic acid were added until the solution became orange. Then 60 ml of ethyl acetate and 60 ml of a saturated NaCl solution were added to the solution. The organic layer was twice extracted with 25 ml of a saturated NaCl solution and dried over sodium sulphate. After evaporation the orange residue was purified by means of column chromatography (eluent chloroform:methanol:glacial acetic acid, 100:1:0.5). The yield was 0.060 g (82%).

Compound 29a $[\alpha^{20}{}_D] = +196°$ (c=0.07 in dioxan), $^1$H-NMR (400 MHz, CDCl$_3$, TMS internal standard): δ=0.20 ppm (9H, s, Si(CH$_3$)$_3$), δ=1.33 ppm (3H, d, J=6.5 Hz, 6'-Me), δ=1.78-2.09 ppm (2H, m, 4'-OH and 2-H$_2$'), δ=2.28 ppm (1H, dd, J=14.7 Hz and J=4.5 Hz, H$_9$(ax)), δ=2.60 ppm (1H, m, H$_9$(eq)), δ=2.99 ppm (1H, d, J=19 Hz, H$_7$(ax)), δ=3.59 ppm (1H, dd, J=19 Hz and J=1.5 Hz, H$_7$(eq)), δ=3.63-3.67 ppm (1H, m, H$_4$'), δ=3.90 ppm (1H, s, 8-OH), δ=4.08 ppm (3H, s, OMe), δ=4.20 ppm (1H, m, H$_3$'), δ=4.33 ppm (1H, q, J=6.5 Hz, H$_5$'), δ=5.21 ppm (1H, m, H$_{10}$), δ=5.54 ppm (1H, br d, J=3.8 Hz, H$_1$'), δ=6.58 ppm (1H, br d, J=8.5 Hz, NH), δ=7.38-8.06 ppm (3h, M, ArH), δ=13.32 ppm (1H, s, ArOH), δ=14.04 ppm (1H, s, ArH).

0.06 g (0.09 mmol) of compound 29a was dissolved in 10 ml of 0.1M NaOH and the reaction mixture was stirred at room temperature and under an argon atmosphere for 30 minutes. The reaction was followed by means of TLC (water:acetic acid:methanol:chloroform, 12:26:54:160). After the reaction the solution was acidified with 1M HCl to pH 9. The neutralized solution was extracted various times with 25 ml of chloroform until the organic layer did not colour anymore. The combined organic layers were washed with water and dried over sodium sulphate. After filtration and evaporation the residue was dissolved in a minimum amount of a solution of chloroform and methanol (9/1). After the addition of 0.15 ml of 0.6M HCl in methanol and 25 ml of diethyl ether, the HCl salt precipitated. After filtering off, 0.024 g (50%) of compound 30a could be isolated.

Compound 30a

Melting point 227°-230° C., $[\alpha^{20}{}_D] = +93°$ (c=0.0475 in dioxan).

Reaction scheme E

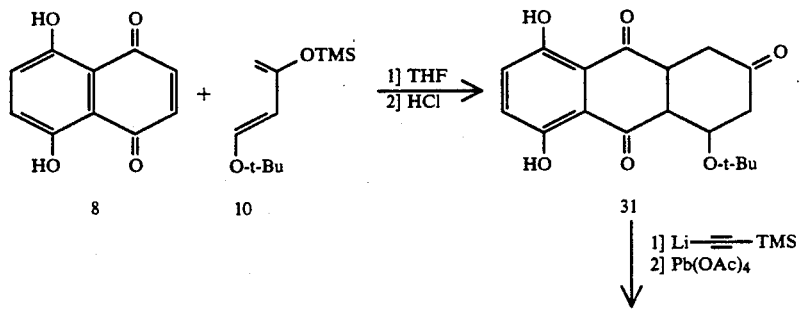

-continued
Reaction scheme E

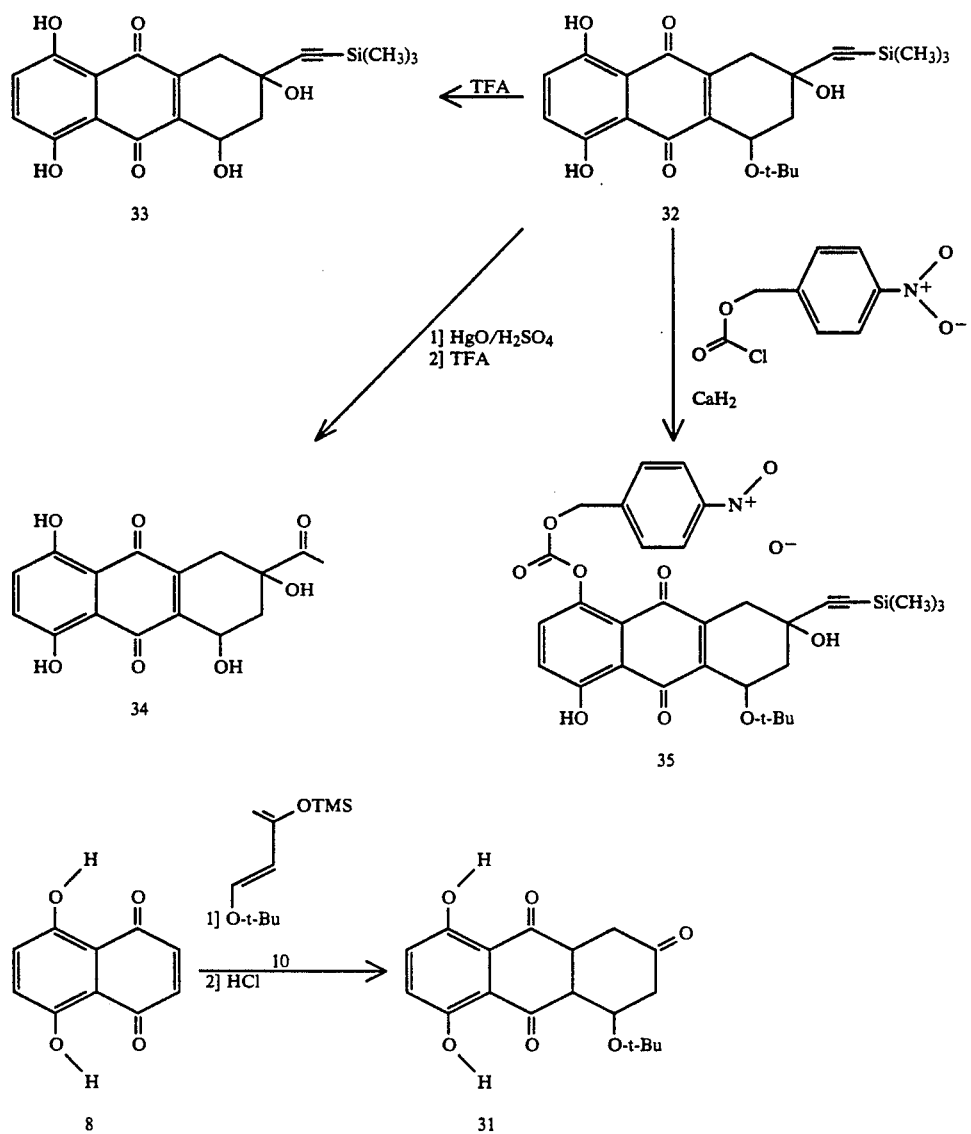

9.0 g of naphthazarin 8 (47 mmol) was dissolved under an argon atmosphere in 150 ml THF which had been distilled over sodium. 14.2 g (66 mmol) of 1-tert-butoxy-3-trimethylsilyloxy-1,3-butadiene (10) were added and then the solution was brought under an argon atmosphere again. The reaction was followed by means of TLC (ethyl acetate:n-hexane 2:5). After one hour the reaction mixture was cooled to 0° C. and 5.75 ml of 1N HCl was added to the solution. The course of the reaction was again followed by means of TLC (ethyl acetate:n-hexane 3:5). After 10 minutes 125 ml of water was added and the solution was extracted with 2×225 ml chloroform. The organic phase was washed with 125 ml of saturated NaCl solution and then dried over anhydrous sodium sulphate. Then after evaporation the residue was dissolved in 300 ml of dried diethyl ether and stirred for one night. After cooling to 0° C. the light-yellow solid was filtered off and washed with cold diethyl ether until the filtrate did not discolour anymore. The yield of compound 31 was 12.1 g (77%). Melting point 180° C.

$^1$H-NMR (90 MHz, CDCl$_3$, TMS internal standard): δ=0.75 ppm (9H, s, C(CH$_3$)$_3$), δ=2.37 ppm (1H, dd, J=7.5 Hz and J=15.6 Hz, CH$_2$), δ=2.58 ppm (2H, d, J=2.5 Hz, CH$_2$), δ=3.33–3.73 ppm (3H, m), δ=4.42–4.50 ppm (1H, m, H$_1$), δ=7.25 ppm (1H, AB, J=8.5 HzArH), δ=7.31 ppm (1H, AB, J=8.5 Hz, ArH), δ=12.1 ppm (1H, s, ArOH), δ=12.30 ppm (1H, s, ArOH).

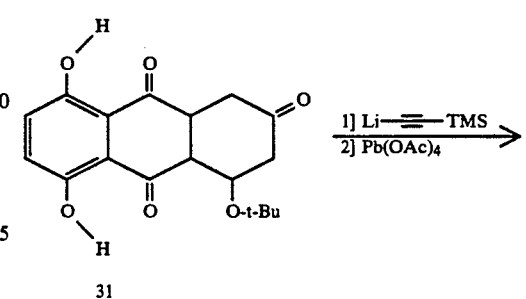

-continued

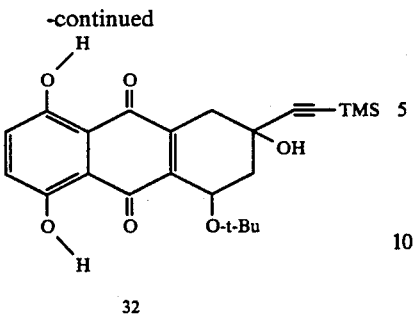

32

6.0 g (61.4 mmol) of trimethylsilyl acetylene was dissolved in 740 ml of sodium-distilled THF in a 1 liter three-neck-flask and cooled under an argon atmosphere to −78° C. 24.7 ml (60.2 mmol) of 2.45M n-butyl lithium was added dropwise to the solution. After stirring at −78° C. for 30 minutes 4.0 g (12.1 mmol) of compound (31) was added. The reaction was followed by means of TLC (ethyl acetate:n-hexane 3:5). After stirring at −78° C. for 3 hours 280 ml of 10% ammonium chloride solution and thereafter 500 ml of water were added. The mixture was extracted with 2×500 ml of chloroform and the collected organic fractions were washed with 500 ml of saturated NaCl solution. After evaporation the residue was dissolved in 100 ml of glacial acetic acid and 5.3 g (12.0 mmol) of lead tetraacetate was added. After stirring for one night the reaction mixture was poured into 400 ml of water and the red solid was filtered off. After rinsing with water the solid was rinsed from the filter with a minimum amount of chloroform and the organic fraction was extracted with successively 100 ml of a saturated NaHCO₃ solution, 2×100 ml of water and 200 ml of a saturated NaCl solution. The organic phase was dried over anhydrous sodium sulphate and evaporated. The compound was purified by means of column chromatography (first red fraction, eluent chloroform). After evaporating the product was stirred in 100 ml of anhydrous diethyl ether for one night, whereafter the red solid (32) could be filtered off (2.6 g, 50%). Melting point 191°–193° C.

¹H-NMR (90 MHz, CDCl₃, TMS internal standard): $\delta=0.18$ ppm (9H, s, Si(CH₃)₃), $\delta=1.33$ ppm (9H, s, C(CH₃)₃), $\delta=1.87$ ppm (1H, dd, J=3.75 Hz and J=14.5 Hz, H₂(ax)), $\delta=2.64$ ppm (1H, d, J=14.5 Hz, H₂(eq)), $\delta=2.77$ ppm (1H, d, J=20 Hz, H₄(ax)), $\delta=3.47$ ppm (1H, d, J=20 Hz, H₄(eq)), $\delta=5.19$ ppm (1H, m, H₁), $\delta=5.57$ ppm (1H, s, OH), $\delta=7.18$ ppm (2H, s, ArH), $\delta=12.56$ ppm (1H, s, ArOH), $\delta=12.69$ ppm (1H, s, ArOH).

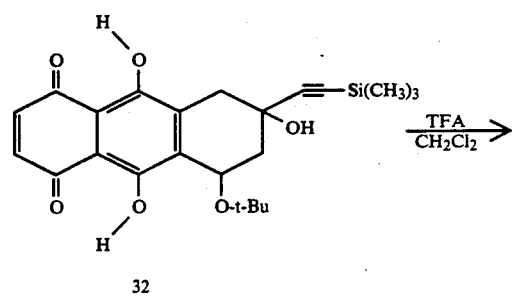

32

-continued

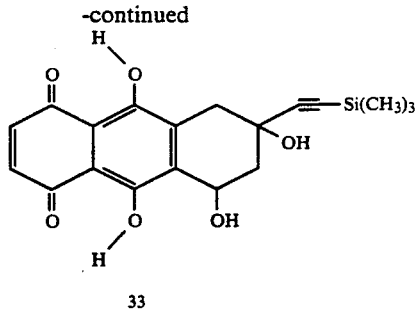

33

1.0 g (2.3 mmol) of 32 was dissolved in 20 ml of trifluoro acetic acid and 30 ml of methylene chloride. The course of the reaction was followed by means of TLC (ethyl acetate:n-hexane, 3:5). After about 10 minutes the starting material had been converted and 100 ml of water was added to the solution. The organic phase was washed with 1×100 ml of a saturated sodium bicarbonate solution, 100 ml of water and 100 ml of a saturated NaCl solution. After recrystallizing in diisopropyl ether 0.6 g (70%) of compound 33 could be isolated.

¹H-NMR (90 MHz, CDCl₃, TMS internal standard): $\delta=0.18$ ppm (9H, s, Si(CH₃)₃), $\delta=2.17$ ppm (1H, dd, J=15 and J=5 Hz, H₂(ax)), $\delta=2.57$ ppm (1H, d, J=15 Hz, H₂(eq)), $\delta=2.83$ ppm (1H, d, J=18.75 Hz, H₄(ax)), $\delta=3.21$ ppm (1H, s, 3-OH), $\delta=3.31$ ppm (1H, d, J=18.75 Hz, H₄(eq)), $\delta=3.68$ (1H, d, J=6.25 Hz, 1-OH), $\delta=5.08$ (1H, m, H₁), $\delta=7.22$ ppm (2H, s, ArH), $\delta=12.47$ ppm (2H, s, ArOH).

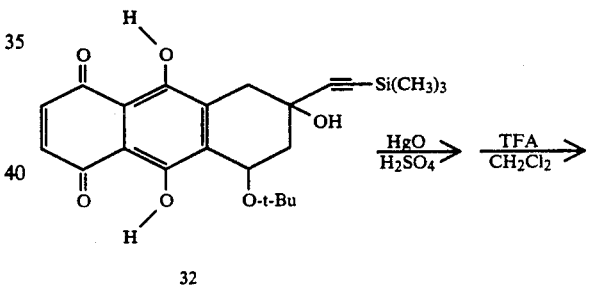

32

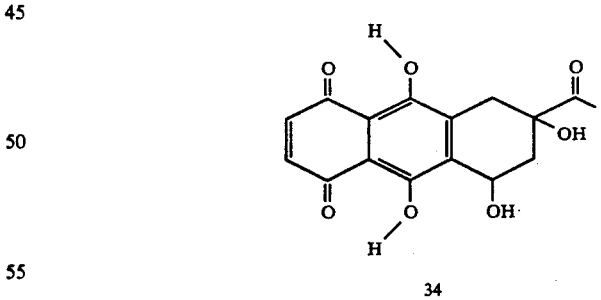

34

1.0 g (2.3 mmol) of 32 was dissolved in 50 ml of THF. 25 ml of 3M sulfuric acid and 0.5 g mercury (II) oxide where added thereto. The solution was stirred at room temperature for 4 hours. Then the reaction mixture was poured into 120 ml of 1M HCl and extracted with chloroform (3×100 ml). The organic phase was dried over anhydrous sodium sulphate and evaporated. Then the crude produkt was dissolved in 60 ml of chloroform and 40 ml of trifluoro acetic acid were added. After stirring at room temperature for 15 minutes, 100 ml of water was added to the solution. The organic phase was washed with 1×100 ml of a saturated sodium bicarbonate solution, 100 ml of water and 100 ml of a saturated NaCl solution. The product was purified by means of column chromatography (column 15 cm, 2.5 cm φ, eluent ethyl acetate:toluene:n-hexane 1:5:5). The yield (34) was 0.45 g (60%) after recrystallization in diisopropyl ether/methylene chloride. Melting point 180°–181° C.

$^1$H-NMR (90 MHz, CDCl$_3$, TMS internal standard):

$\delta$=2.06 ppm (1H, dd, J=14.5 Hz and J=5 Hz, H$_2$(ax)), $\delta$=2.32 ppm (1H, dt, J=14.5 Hz, H$_2$(eq)), $\delta$=2.40 ppm (3H, s, CH$_3$), $\delta$=2.77 ppm (1H, d, J=19.5 Hz and J=1.2 Hz, H$_4$(ax)), $\delta$=3.08 ppm (1H, d, J=19.5 Hz and J=2.0 Hz, H$_4$(eq)), $\delta$=3.73 ppm (1H, d, J=6.5 Hz, 1-OH), $\delta$=4.46 ppm (1H, s, 3-OH), $\delta$=5.17 ppm (1H, m, H$_1$), $\delta$=7.24 ppm (2H, s, ArH), $\delta$=12.47 ppm (2H, s, ArOH).

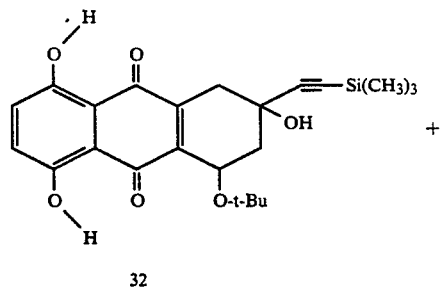

32

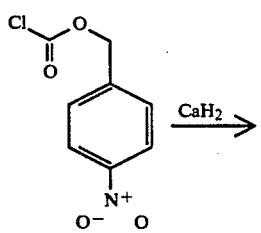

-continued

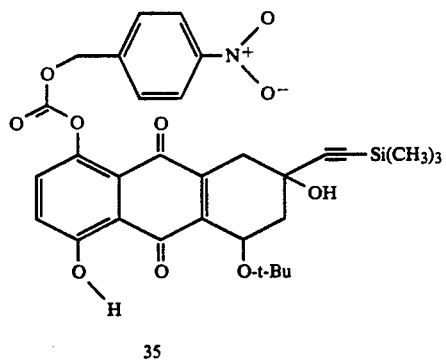

35

5.0 g (11.7 mmol) of compound 32 and 3.0 g (14.0 mmol) of paranitrobenzyloxycarbonyl chloride were dissolved in 150 ml sodium-distilled THF in a vibration vessel which belonged to a direct immersion sonic horn. To this solution 0.5 g (11.9 mmol) of crushed CaH$_2$ was added and the solution was cooled to 0° C. The reaction mixture was caused to vibrate by means of a direct immersion sonic horn for 4 hours. Then the solution was transferred to a 250 ml flask which was placed in an ultrasonic cleaning bath and sonicated at 60° C. for 24 hours. The course of the reaction can be followed by means of TLC (ethyl acetate:n-hexane 2:5); the colour of the solution changes from red tot yellow. After the reaction the reaction mixture was poured into 500 ml of a 5% NaH$_2$PO$_4$ solution en extracted with 500 ml of chloroform. The organic phase was dried over anhydrous sodium sulphate and evaporated. The crude reaction mixture was purified by means of column chromatography (eluent ethyl acetate:n-hexane 1:4) and after evaporating stirred in 50 ml of diisopropyl ether. The yield (35) was 5.0 g (71%). Melting point 164° C.

$^1$H-NMR (400 MHz, CDCl$_3$, TMS internal standard): $\delta$=0.20 ppm (9H, s, Si(CH$_3$)$_3$), $\delta$=1.36 ppm (9H, s, C(CH$_3$)$_3$), $\delta$=1.90 ppm (1H, dd, J=3.75 and H=14.5 Hz, H$_2$(ax)), $\delta$=2.67 ppm (1H, d, J=14.5 Hz, H$_2$(eq)), $\delta$=2.77 ppm (1H, d, J=20 Hz, H$_4$(ax)), $\delta$=3.47 ppm (1H, d, J=20 Hz, H$_4$(eq)), $\delta$=5.21 ppm (1H, s, H$_1$), $\delta$=5.43 ppm (2H, s, CH$_2$), $\delta$=5.54 ppm (1H, s, 3-OH), $\delta$=7.33 ppm (2H, dd, H$_6$+H$_7$), $\delta$=7.69 ppm (2H, AB, J=8.6 Hz, ArH), $\delta$=8.29 ppm (2H, AB, J=8.6 Hz, ArH), $\delta$=12.47 ppm (1H, s, ArOH).

Reaction scheme F
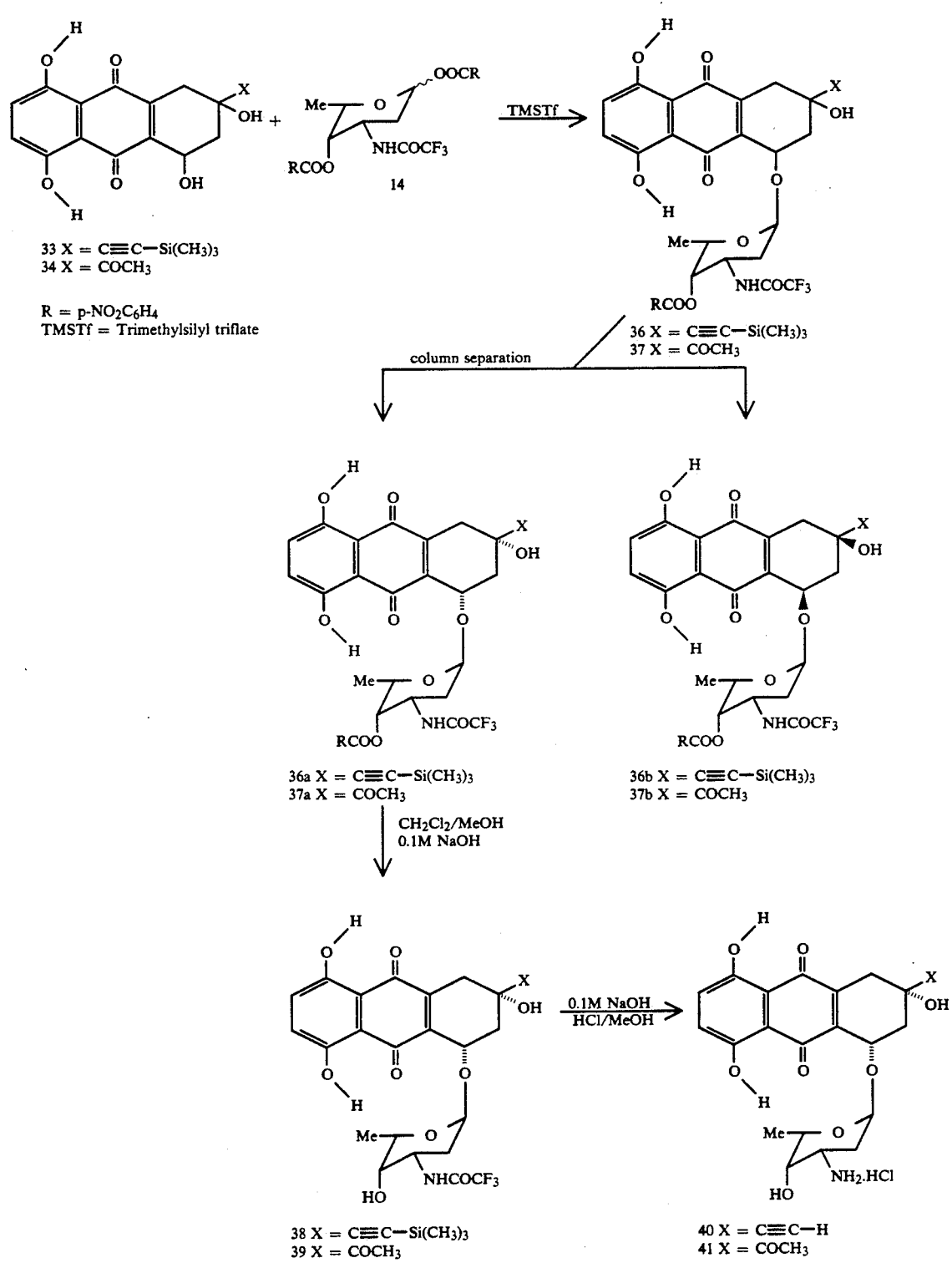

-continued
Reaction scheme F

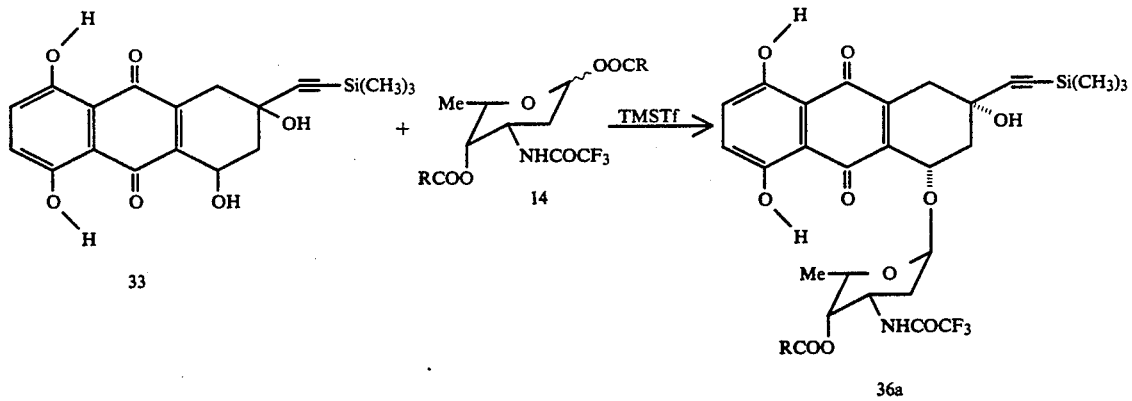

0.48 ml (2.48 mmol) of trimethylsilyl triflate was added to a suspension of 0.628 g of 14 (1.16 mmol) and 4 g of 4 Å molecular sieve in a mixture of 48 ml of methylenen chloride and 40 ml of diethylether (both distilled over $CaH_2$ and sodium, respectively) at $-30°$ C. and under an argon atmosphere. The solution was stirred at 0° C. for 0.5 hour until the solution had become clear. Then the solution was cooled to $-15°$ C. and 0.342 g (0.92 mmol) of 33, dissolved in 100 ml of methylene chloride, was added. The reaction mixture was maintained at $-15°$ C. during the addition and then stirred at $-15°$ C. for 4 hours. The course of the reaction was followed by means of TLC (eluent ethyl acetate:benzene, 1:4). After all the starting material had been converted, the reaction mixture was poured into a solution of 400 ml of saturated sodium bicarbonate while vigorously stirring. The organic layer was separated and then washed with 200 ml of water and 200 ml of a saturated NaCl solution. After drying over anhydrous sodium sulphate and evaporating, the compounds 36a and 36b were separated by means of preparative TLC (eluent ethyl acetate:benzene, 1:4). After evaporation of the eluent and treatment with a small amount of n-hexane, 0.175 g (25%) of 36a could be isolated. $[\alpha^{20}{}_2D] = -100°$, melting point 145°–147° C.

2.15 ml of a 0.1M NaOH solution was added to a stirred solution of 0.16 g (0.21 mmol) of 36a in 1.4 ml of methylene chloride and 80 ml methanol at 0° C. and under an argon atmosphere. The deep purple solution was stirred at 0° C. for 20 minutes and the course of the reaction was followed by means of TLC (methylene chloride:acetone, 9:1). After the reaction a few drops of glacial acetic acid were added until the solution became orange. Then 100 ml of ethyl acetate and 100 ml of a saturated NaCl solution was added to the solution. The organic layer was twice extracted with 50 ml of a saturated NaCl solution and dried over anhydrous sodium sulphate. After evaporation the orange residue was purified by means of column chromatography (eluent chloroform:methanol:acetic acid, 40:1:0.4). The yield of 38 was 0.050 g (39%). $[\alpha^{20}{}_D] = +56.7°$.

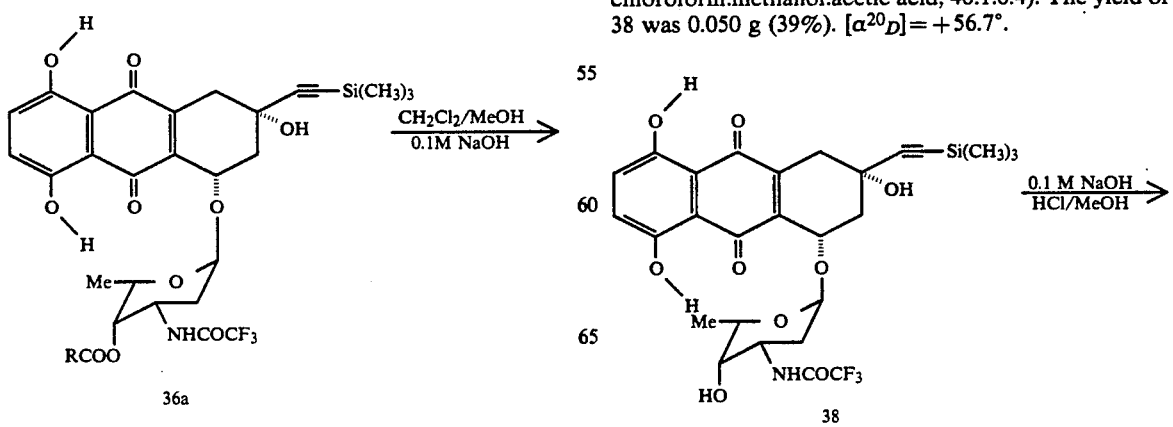

-continued

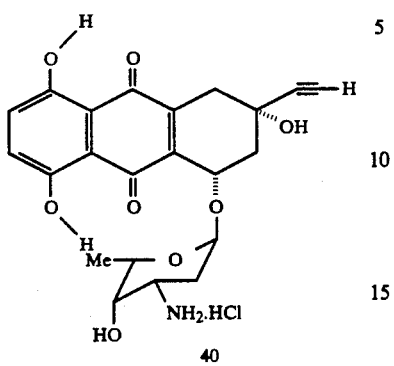

40

To the solution of 0.050 g (0.08 mmol) of 38 in 1 ml of acetone 10 ml of 0.1M NaOH was added and the reaction mixture was stirred at room temperature and under an argon atmosphere for 30 minutes. The reaction was followed by means of TLC (water:acetic acid:methanol:chloroform, 12:26:54:160). After the reaction the solution was acidified with 1M HCl to pH 8. The neutralized solution was extracted a number of times with 50 ml of chloroform until the organic layer no longer showed a colour. The combined organic layers were washed with water and dried over anhydrous sodium sulphate. After filtration and evaporation the residue was dissolved in a minimum amount of a solution of chloroform and methanol (9/1). After the addition of 0.25 ml of 0.6M HCl in methanol and 25 ml of diethylether the HCl salt 40 precipitated. After filtering off, 0.018 g (46%) of compound 40 could be isolated.

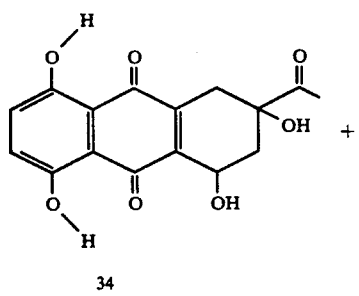

34

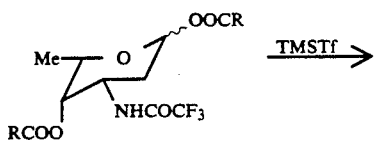

14

-continued

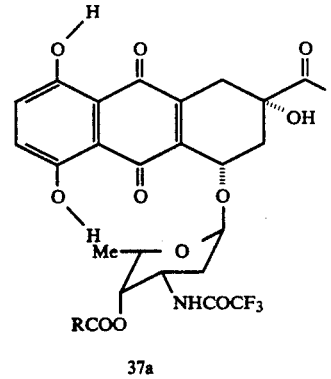

37a 0.42 ml (2.17 mmol) of trimethylsilyl triflate was added to a suspension of 0.542 g of 14 (1.00 mmol) and 3.2 g of 4 Å molecular sieve in a mixture of 40 ml of methylene chloride and 34 ml of diethylether (both distilled over $CaH_2$ and sodium, respectively) at $-30°$ C. and under an argon atmosphere. The solution was stirred at 0° C. for 0.5 hour until the solution was clear. Then the solution was cooled to $-20°$ C. and 0.200 g (0.63 mmol) of 34, dissolved in 80 ml of methylene chloride, was added. The reaction mixture was maintained at $-15°$ C. during the addition and then stirred at $-20°$ C. for 4 hours. The course of the reaction was followed by means of TLC (eluent acetone:methylene chloride, 1:39). After all the starting material had been converted, the reaction mixture was poured into a solution of 250 ml of saturated sodium bicarbonate which was stirred vigorously. The organic layer was separated and then washed with 150 ml of water and 150 ml of a saturated NaCl solution. After drying over anhydrous sodium sulphate and evaporation, the compounds 37a and 37b were separated by means of preparative TLC (eluent acetone:methylene chloride, 1:39). After evaporation of the eluent and treatment with a small amount of n-hexane 0.120 g (28%) of 37a could be isolated. Melting point 150°–152° C., $[\alpha^{20}_D] = -93.3°$.

$^1$H-NMR (400 MHz, $CDCl_3$, TMS internal standard):
$\delta = 1.26$ ppm (3H, d, J=6.5 Hz, 6'-Me), $\delta = 2.03$–2.19 ppm (2H, m, 2-$H_{2'}$ and $H_8$(ax)), $\delta = 2.31$ ppm (1H, m, $H_8$(eq)), $\delta = 2.43$ ppm (3H, s, Me), $\delta = 2.88$ ppm (1H, d, J=18.5 Hz, $H_{10}$(ax)), $\delta = 3.16$ ppm (1H, d, J=18.5 Hz, $H_{10}$(eq)), $\delta = 4.14$ ppm (1H, br s, 9-OH), $\delta = 4.40$–4.51 ppm (2H, m, $H_{3'}$ and $H_{5'}$), $\delta = 5.22$ ppm (1H, m, $H_7$), $\delta = 5.48$ ppm (1H, br s, $H_{4'}$), $\delta = 5.67$ ppm (1H, br s, $H_{1'}$), $\delta = 6.33$ ppm (1H, br d, J=7.5 Hz, NH), $\delta = 7.26$ ppm (2H, s, ArH), $\delta = 8.27$–8.36 ppm (4H, m, ArH), $\delta = 12.51$ ppm (1H, s, ArOH), $\delta = 12.59$ ppm (1H, s, ArH).

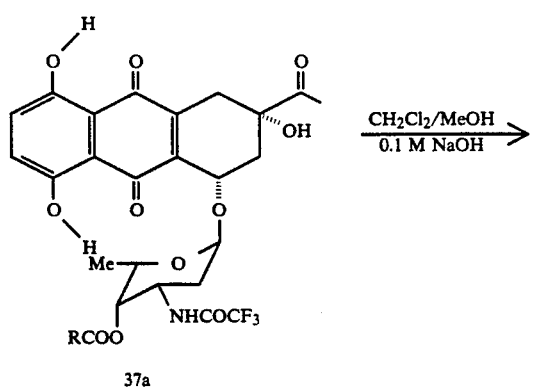

37a

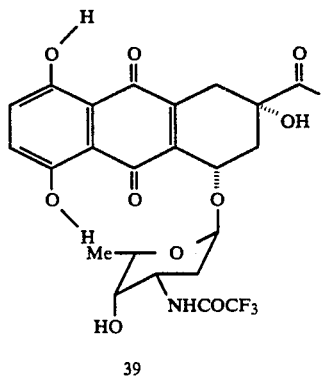

39

1.6 ml of a 0.1M NaOH solution was added to a stirred solution of 0.11 g (0.16 mmol) of 37a in 1 ml of methylene chloride and 60 ml of methanol at 0° C. and under an argon atmosphere. The deep purple solution was stirred at 0° C. for 10 minutes and the course of the reaction was followed by means of TLC (methylene chloride:acetone, 9:1). After the reaction a few drops of glacial acetic acid were added until the solution became orange. Then 75 ml of ethyl acetate and 75 ml of a saturated NaCl solution were added to the solution. The organic layer was twice extracted with 50 ml of a saturated NaCl solution and dried over anhydrous sodium sulphate. After evaporation the orange residue was purified by means of column chromatography (eluent chloroform:methanol:-acetic acid, 40:1:0.4). The yield of 39 was 0.055 g (64%). $[\alpha^{20}_D] = +88.6°$.

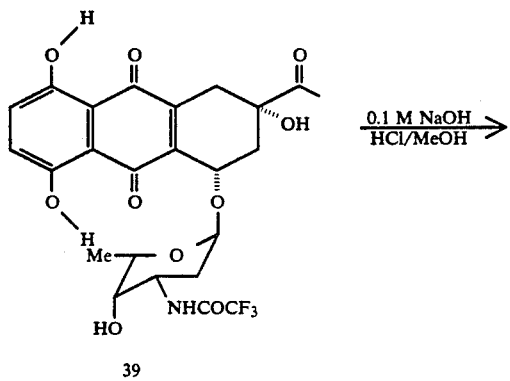

39

-continued

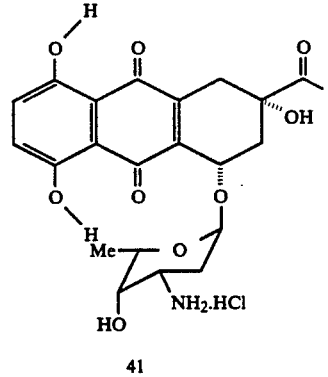

41

To the solution of 0.053 g (0,098 mmol) of 39 in 1 ml of acetone 10 ml of 0.1M NaOH was added and the reaction mixture was stirred at room temperature and under an argon atmosphere for 10 minutes. The reaction was followed by means of TLc (water:acetic acid:methanol:chloroform, 12:26:54:160). After the reaction the solution was acidified with 1M HCl to pH 8. The neutralized solution was extracted several times with 50 ml of chloroform until the organic layer no longer showed a colour. The combined organic layers were washed with water and dried over anhydrous sodium sulphate. After filtration and evaportion the residue was dissolved in a minimum amount of a solution of chloroform and methanol (9/1). After the addition of 0.25 ml of 0.6M HCl in methanol and 25 ml of diethylether the HCl salt 41 precipitated. After filtering off, 0.020 g (42%) of compound 41 could be isolated.

Reaction scheme G

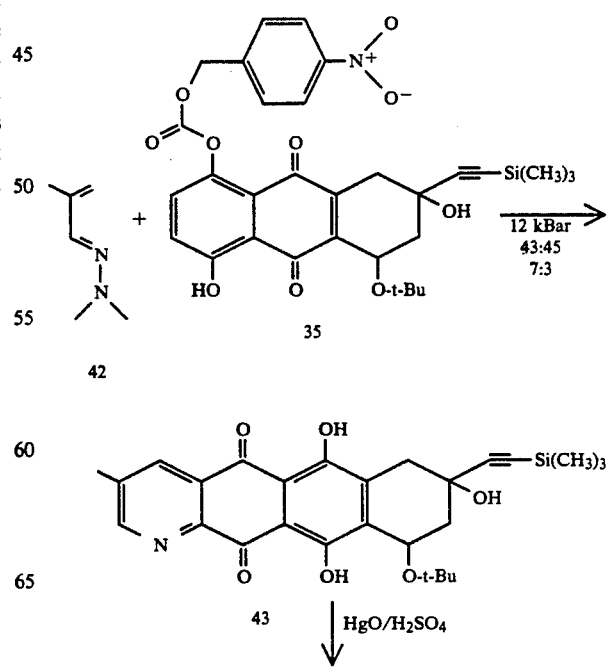

-continued
Reaction scheme G

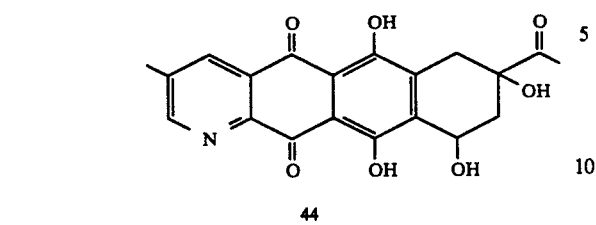

44

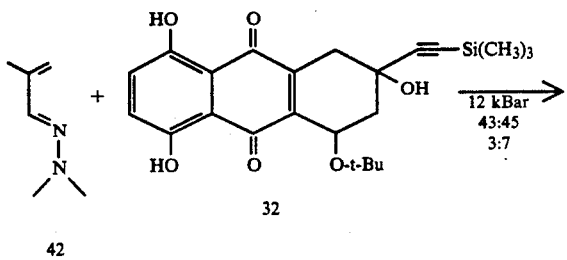

42

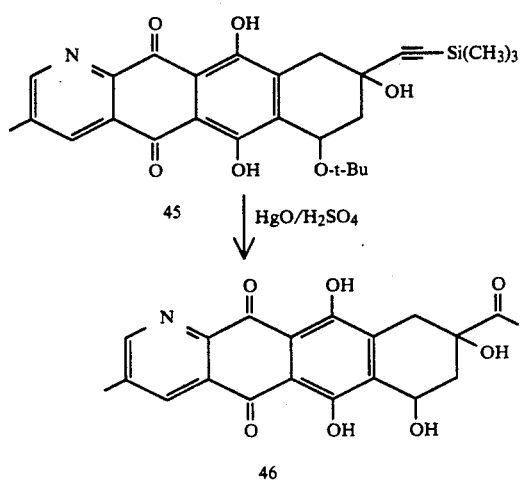

45

46

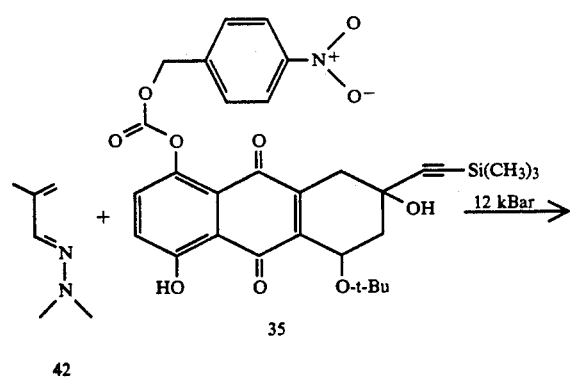

35

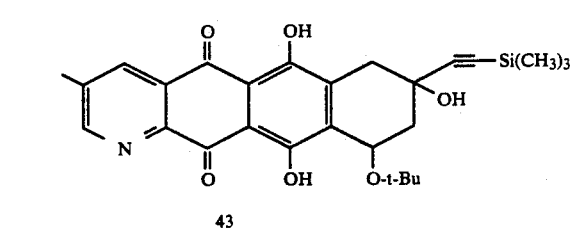

43

-continued
Reaction scheme G

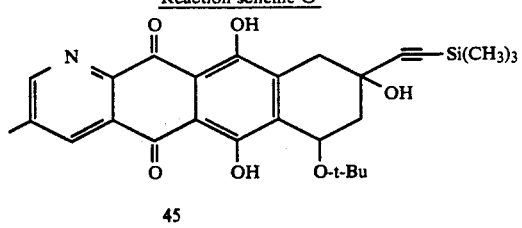

45

43:45, 7:3

1.5 g (2.5 mmol) of compound 35 was dissolved in 10 ml of methylene chloride. 0.75 g (6.6 mmol) of 1-dimethylamino-3-methyl-1-aza-1,3-butadiene 42 was added. The solution was distributed over 2 7.5 ml high pressure-vessels and supplemented with methylene chloride. A pinch of hydroquinone was added to the solution. The vessels were maintained under high pressure (12 kBar) at room temperature for 16 hours. The reaction mixture was evaporated and the residue stirred in 20 ml of anhydrous diethylether. The orange solid was filtered off and purified by means of column chromatography (20 cm, $\phi$=4 cm, eluent 1% methanol in methylene chloride). The yield was 0.26 g (22%) of compound 43. Also 0.11 g (9%) of compound 45 could be isolated.

Compound 43: Melting point 229°–231° C.

$^1$H-NMR (400 MHz, CDCl$_3$, TMS internal standard): $\delta$=0.20 ppm (9H, s, Si(CH$_3$)$_3$), $\delta$=1.41 ppm (9H, s, C(CH$_3$)$_3$), $\delta$=2.01 ppm (1H, d, J=14.5 Hz, H$_9$(ax)), $\delta$=2.59 ppm (3H, s, CH$_3$), $\delta$=2.76 ppm (1H, d, J=14.5 Hz, H$_9$(eq)), $\delta$3.05 ppm (1H, d, J=20 Hz, H$_7$(ax)), $\delta$=3.67 ppm (1H, d, H=20 Hz, H$_7$(eq)), $\delta$=5.37 ppm (1H, brs, H$_{10}$), $\delta$=5.91 ppm (1H, s, OH), $\delta$=8.39 ppm (1H, s, ArH), $\delta$=8.91 ppm (1H, s, ArH), $\delta$=13.23 ppm (1H, s, ArOH), $\delta$=13.80 ppm (1H, s, ArOH).

Compound 45: Melting point 258°–260° C.

$^1$H-NMR (400 MHz, CDCl$_3$, TMS internal standard): $\delta$=0.22 ppm (9H, s, Si(CH$_3$)$_3$), $\delta$=1.41 ppm (9H, s, C(CH$_3$)$_3$), $\delta$=2.01 ppm (1H, d, J=14.5 Hz, H$_8$(ax)), $\delta$=2.59 ppm (3H, s, CH$_3$), $\delta$=2.76 ppm (1H, d, J=14.5 Hz, H$_8$(eq)), $\delta$=3.08 ppm (1H, d, J=20 Hz, H$_{10}$(ax)), $\delta$=3.70 ppm (1H, d, J=20 Hz, H$_{10}$(eq)), $\delta$=5.37 ppm (1H, brs, H$_7$), $\delta$=5.87 ppm (1H, s, OH), $\delta$=8.44 ppm (1H, s, ArH), $\delta$=8.94 ppm (1H, s, ArH), $\delta$=13.46 ppm (1H, s, ArOH), $\delta$=13.56 ppm (1H, s, ArOH).

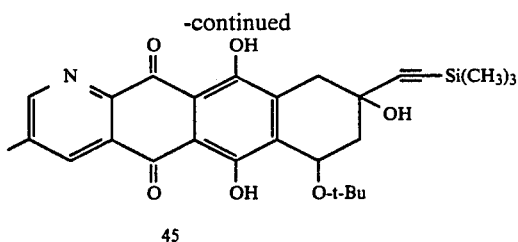

43:45, 3:7

1.07 g (2.5 mmol) of compound 32 was dissolved in 10 ml of methylene chloride. 0.75 g (6.6 mmol) of 1-dimethylamino-3-methyl-1-aza-1,3-butadiene 42 was added. The solution was distributed over 2 7.5 ml high pressure-vessels and supplemented with methylene chloride. To the solution a pinch of hydroquinone was added. The vessels were maintained under high pressure (12 kBar) at room temperature for 16 hours. Then the reaction mixture was evaported and the residue was stirred in 20 ml of anhydrous diethyl ether. The orange solid was filtered off and purified by means of column chromatography (20 cm, $\phi=4$ cm, eluent 1% methanol in methylene choride). The yield was 0.27 g (22%) of compound 45. Also 0.10 g (8%) of compound 43 could be isolated.

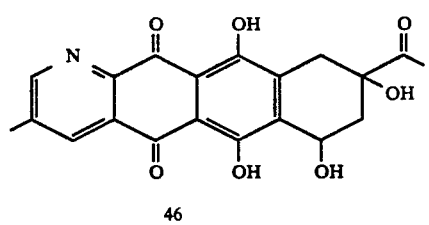

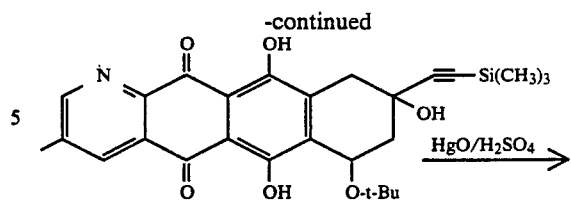

0.57 g (1.15 mmol) of compound 43/45 was dissolved in 22 ml of THF and 11 ml of 6N $H_2SO_4$ solution and 0.3 g (1.38 mmol) of HgO was added thereto. The reaction mixture was caused to vibrate in an ultrasonic bath for 24 hours. Then the reaction mixture was poured into 75 ml of 1M HCl solution and extracted with chloroform (3×50 ml). The organic phase was dried over anhydrous sodium sulphate and after evaporation purified by means of column chromatography (eluent chloroform:methanol:acetic acid 40:1:0.4). The yield was 0.38 g (86%).

Compound 44: Melting point 163°–165° C.

$^1$H-NMR (400 MHz, CDCl$_3$, TMS internal standard): $\delta=2.19$ ppm (1H, dd, J=14.5 Hz and J=4.9 Hz, H$_9$(ax)), $\delta=2.35$ ppm (1H, dt, J=14.5 Hz, H$_9$(eq)), $\delta=2.44$ ppm (3H, s, CH$_3$), $\delta=2.60$ ppm (3H, s, CH$_3$), $\delta=2.99$ ppm (1H, d, J=18.7 Hz, H$_7$(ax)), $\delta=3.22$ ppm (1H, dd, H=18.7 Hz and J=2.2 Hz, H$_7$(eq)), $\delta=3.77$ ppm (1H, d, J=5 Hz, 10-OH), $\delta=4.54$ ppm (1H, s, 8-OH), $\delta=5.36$ ppm (1H, brs, H$_{10}$), $\delta=8.46$ ppm (1H, d, J=2 Hz, ArH), $\delta=8.96$ ppm (1H, d, J=2 Hz, ArH), $\delta=13.42$ ppm (1H, s, ArOH), $\delta=13.68$ ppm (1H, s, ArOH).

Compound 46: Melting point 197°–199° C.

$^1$H-NMR (400 MHz, CDCl$_3$, TMS internal standard): $\delta=2.20$ ppm (1H, dd, J=14.5 Hz and J=4.8 Hz, H$_8$(ax)), $\delta=2.39$ ppm (1H, dt, J=14.5 Hz, H$_8$(eq)), $\delta=2.44$ ppm (3H, s, CH$_3$), $\delta=2.60$ ppm (3H, s, CH$_3$), $\delta=3.00$ ppm (1H, d, J=18.7 Hz, H$_{10}$(ax)), $\delta=3.24$ ppm (1H, dd, J=18.7 Hz and J=2.1 Hz, H$_{10}$(eq)), $\delta=3.84$ ppm (1H, d, J=6.5 Hz, 7-OH), $\delta=4.51$ ppm (1H, s, 9-OH), $\delta=5.34$ ppm (1H, brs, H$_7$), $\delta=8.47$ ppm (1H, d, J=2 Hz, ArH), $\delta=8.96$ ppm (1H, d, J=2 Hz, ArH), $\delta=13.41$ ppm (1H, s, ArOH), $\delta=13.43$ ppm (1H, d, ArOH).

Reaction scheme H

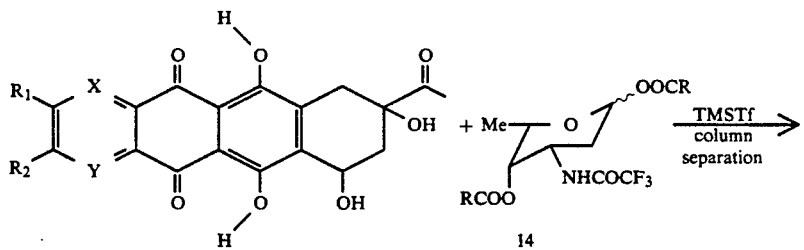

44 X = C, Y = N, R₁ = Me, R₂ = H
46 X = N, Y = C, R₁ = H, R₂ = Me

TMSTf = Trimethylsilyltriflate
R = p-NO₂C₆H₄

-continued
Reaction scheme H

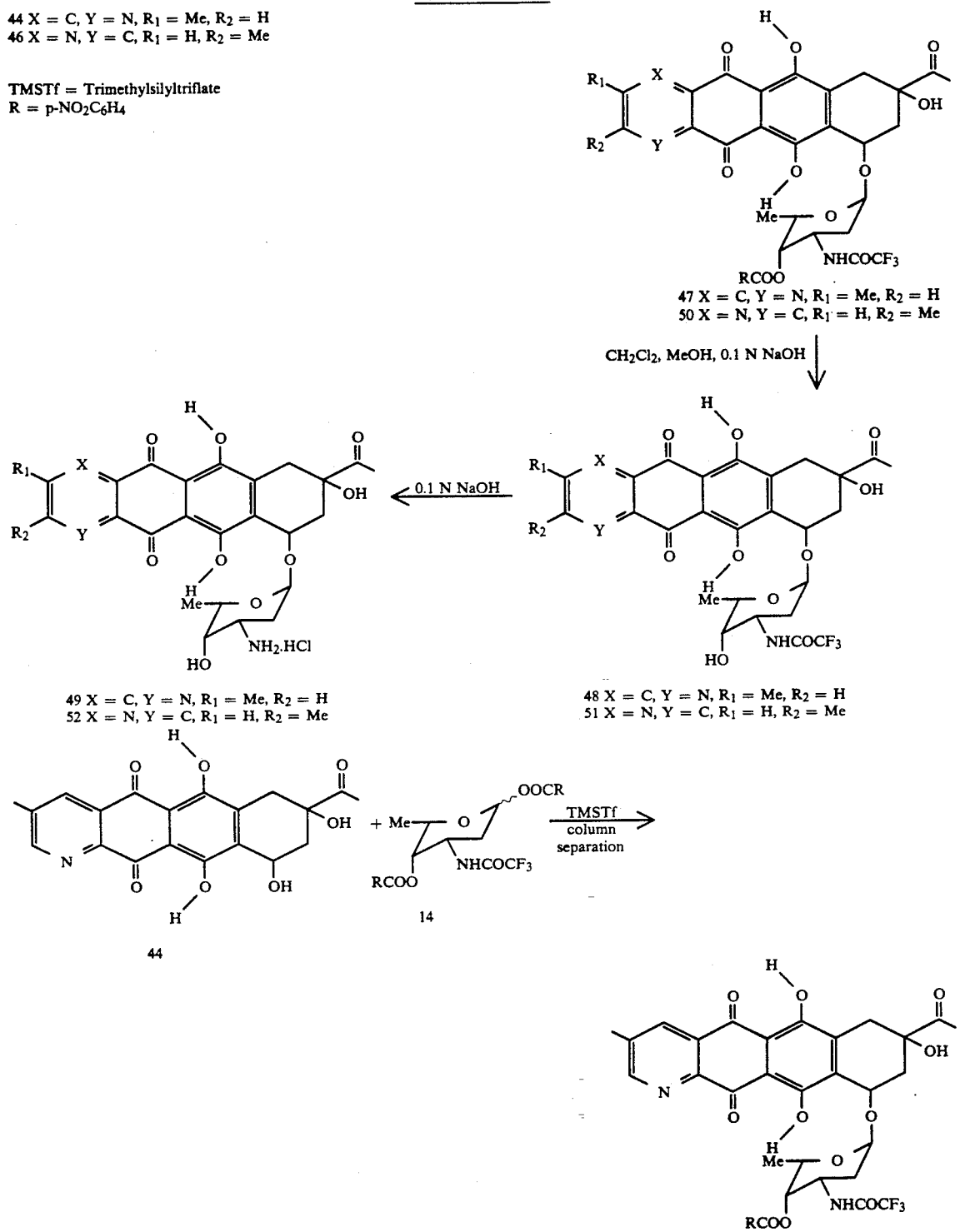

0.27 ml of trimethylsilyltriflate (1.4 mmol) was added to a suspension of 0.36 g of 14 (0.66 mmol) and 2 g of 4 Å molecular sieve in a mixture of 27 ml of methylene chloride and 23 ml of diethyl ether (both distilled over CaH₂ and sodium, respectively) at −30° C. and under an argon atmosphere. The solution was stirred at 0° C. for 1 hour until the solution became clear. Then the solution was cooled to −15° C. and 0.200 g (0.52 mmol) of 44, dissolved in 55 ml of methylene chloride, was added. The reaction mixture was maintained at −15° C. during the addition and then stirred at −15° C. for 3 hours. The course of the reaction was followed by means of TLC (eluent ethyl acetate:benzene, 1:4). After all starting material had been converted, the reaction mixture was poured into a solution of 350 ml of saturated sodium bicarbonate while vigorously stirring. The organic layer was separated and then washed with 100 ml of water and 100 ml of a saturated NaCl solution. After drying over anhydrous sodium sulphate and evaporating, compound 47 was purified by means of preparative TLC (eluent methylene chloride:acetone, 9:1). After evaporation of the eluent and treatment with a small amount of n-hexane 0.165 g (42%) of 47 could be isolated.

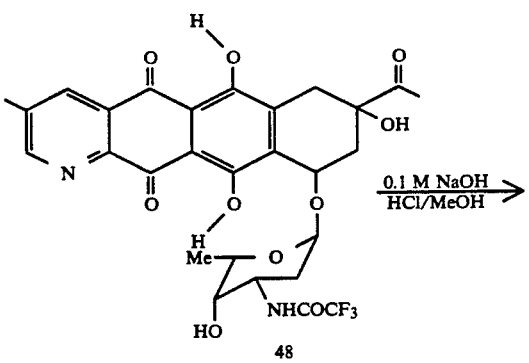

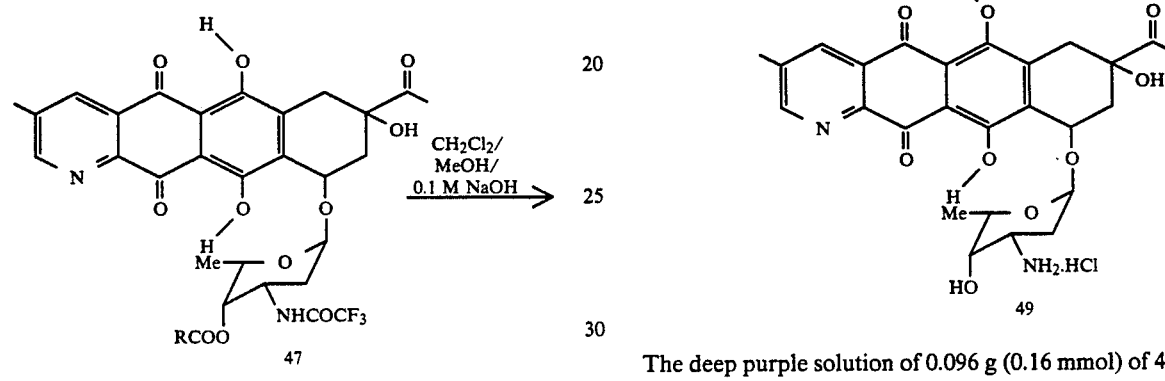

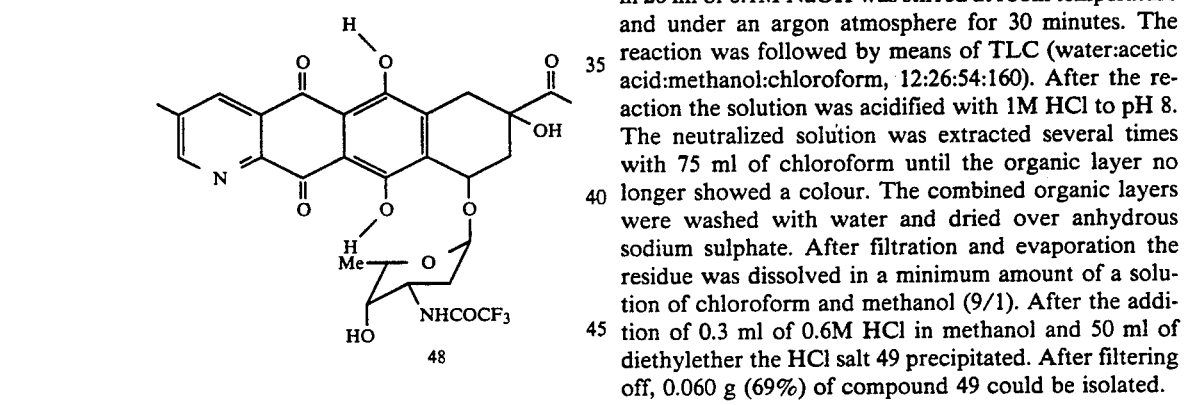

4.0 ml of a 0.1M NaOH solution was added to a solution of 0.300 g (0.4 mmol) of 47 in 3.9 ml of methylene chloride and 150 ml of methanol at 0° C. and under an argon atmosphere. The deep purple solution was stirred at 0° C. for 20 minutes and the course of the reaction was followed by means of TLC (methylene chloride-:acetone, 9:1). After the reaction a few drops of glacial acetic acid were added until the solution became orange. Then 240 ml of ethyl acetate and 240 ml of a saturated NaCl solution were added to the solution. The organic layer was twice extracted with 80 ml of a saturated NaCl solution and dried over anhydrous sodium sulphate. After evaporation the orange residue was purified by means of preparative TLC (eluent 5% methanol in chloroform). The yield was 0.106 g (44%).

The deep purple solution of 0.096 g (0.16 mmol) of 48 in 20 ml of 0.1M NaOH was stirred at room temperature and under an argon atmosphere for 30 minutes. The reaction was followed by means of TLC (water:acetic acid:methanol:chloroform, 12:26:54:160). After the reaction the solution was acidified with 1M HCl to pH 8. The neutralized solution was extracted several times with 75 ml of chloroform until the organic layer no longer showed a colour. The combined organic layers were washed with water and dried over anhydrous sodium sulphate. After filtration and evaporation the residue was dissolved in a minimum amount of a solution of chloroform and methanol (9/1). After the addition of 0.3 ml of 0.6M HCl in methanol and 50 ml of diethylether the HCl salt 49 precipitated. After filtering off, 0.060 g (69%) of compound 49 could be isolated.

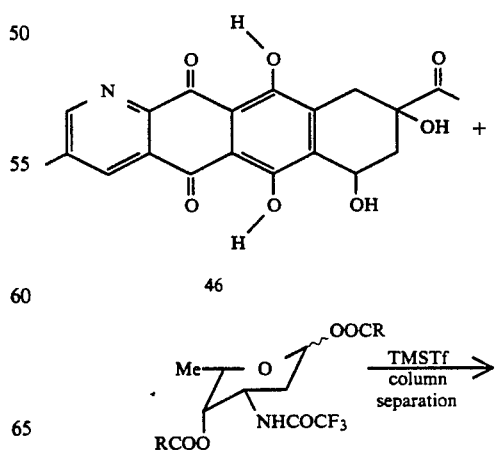

-continued

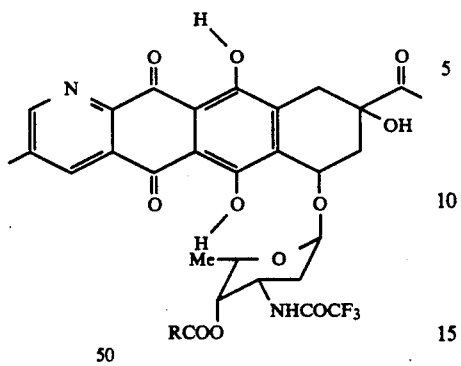
50

0.21 ml of trimethylsilytriflate (1.11 mmol) was added to a suspension of 0.283 g of 14 (0.52 mmol) and 3.5 g of 4 Å molecular sieve in a mixture of 22 ml of methylene chloride and 18 ml of diethyl ether (both distilled over CaH₂ and sodium, respectively) at −30° C. and under an argon atmosphere. The solution was stirred at 0° C. for 1 hour until the solution became clear. Then the solution was cooled to −15° C. and 0.155 g (0.41 mmol) of 46, dissolved in 45 ml of methylene chloride, was added. The reaction mixture was maintained at −15° C. during the addition and then stirred at −15° C. for 3 hours. The course of the reaction was followed by means of TLC (eluent ethyl acetate:benzene, 1:4). After all the starting material had been converted, the reaction mixture was poured into a solution of 250 ml of saturated sodium bicarbonate while vigorously stirring. The organis layer was separated and then washed with 100 ml of water and 100 ml of a saturated NaCl solution. After drying over anhydrous sodium sulphate and evaporation, compound 50 was purified by means of preparative TLC (eluent methylene chloride:acetone, 9:1). After evaporation of the eluent and treatment with a small amount of n-hexane, 0.126 g (41%) of 50 could be isolated.

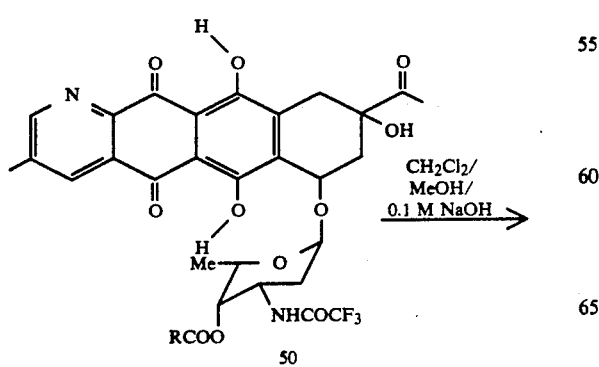
50

2.7 ml of a 0.1M NaOH solution was added to a solution of 0.207 g (2.7 mmol) of 50 in 16 ml of methylene chloride and 110 ml of methanol at 0° C. and under an argon atmosphere. The deep purple solution was stirred at 0° C. for 20 minutes and the course of the reaction was followed by means of TLC (methylene chloride:acetone, 9:1). After the reaction a few drops of glacial acetic acid were added until the solution became orange. Then 150 ml of ethyl acetate and 150 ml of a saturated NaCl solution was added to the solution. The organic layer was twice extracted with 50 ml of a saturated NaCl solution and dried over anhydrous sodium sulphate. After evaporation the orange residue was purified by means of preparative TLC (eluent 5% methanol in chloroform). The yield was 0.075 g (45%).

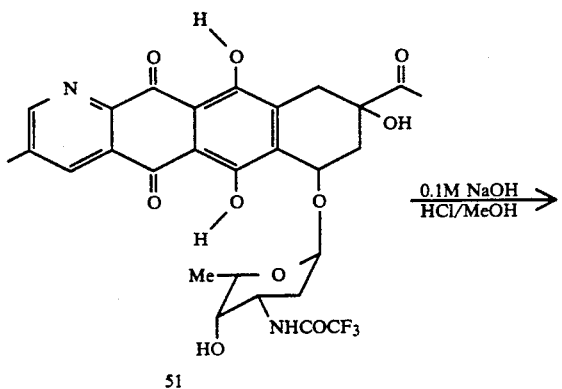
51

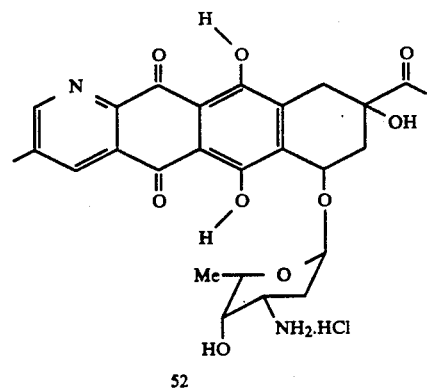
52

The deep purple solution of 0.063 g (0.10 mmol) of 51 in 12 ml of 0.1M NaOH was stirred at room temperature and under an argon atmosphere for 30 minutes. The reaction was followed by means of TLC (water:acetic acid: methanol:chloroform, 12:26:54:160). After the reaction the solution was acidified with 1M HCL to pH 8. The neutralized solution was extracted several times with 50 ml of chloroform until the organic layer no longer showed a colour. The combined organic layers were washed with water and dried over anhydrous sodium sulphate. After filtration and evaporation the residue was dissolved in a minimum amount of a solution of chloroform and methanol (9/1). After the addition of 0.2 ml of 0.6M HCl in methanol and 25 ml of diethylether, the HCl salt 52 precipitated. After filtering off, 0.040 g (70%) of compound 52 could be isolated.

We claim:

1. A compound of formula (1):

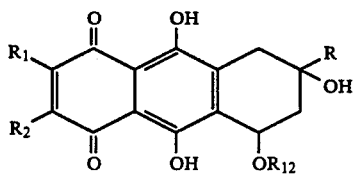
(1)

wherein
R is —COCH$_3$ or —C≡C—R$_4$;
R$_4$ is H or —Si(CH$_3$)$_3$;
R$_1$ and R$_2$ represent H or together form a group —CR$_5$=CR$_6$—CR$_7$=CR$_8$—, —CR$_9$=CR$_{10}$—CR$_{11}$=N— or —N=CR$_9$—CR$_{10}$=CR$_{11}$;
each of the symbols R$_5$, R$_6$, R$_7$, and R$_8$ represents H or a C$_1$-C$_3$ alkyl group, a C$_1$-C$_3$ alkoxy group or an —OH group;
each of the symbols R$_9$, R$_{10}$ and R$_{11}$ represents H or a C$_1$-C$_3$ alkyl group;
R$_{12}$ is H or

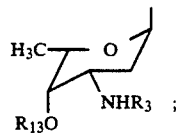

R$_3$ is H or —COCF$_3$;
R$_{13}$ is H or

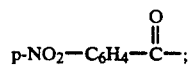

or a pharmaceutically acceptable acid addition salt thereof;
with the exclusion of compounds where
R is —COCH$_3$ or —C≡CH and R$_1$ and R$_2$ form a group —CR$_5$=CR$_6$—CR$_7$=CR$_8$—, or an acid addition salt of an excluded compound.

2. A compound in accordance with claim 1, wherein R$_{12}$ is

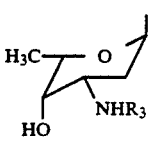

wherein R$_3$ is as defined in claim 1.

3. A compound in accordance with claim 1, wherein R$_{12}$ is

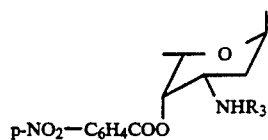

wherein R$_3$ is as defined in claim 1.

4. A compound in accordance with claim 1 wherein R$_{12}$ is H.

5. A compound in accordance with claim 1 having the formula 2:

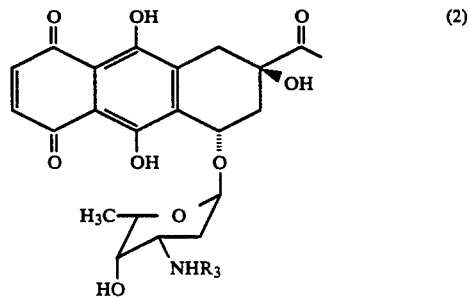
(2)

wherein R$_3$ is as defined in claim 1; or a pharmaceutically acceptable acid addition salt thereof.

6. A compound in accordance with claim 1 having the formula 3:

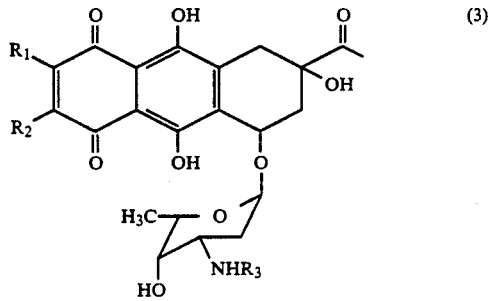
(3)

wherein R$_1$ and R$_2$ together form a group —CH=C(CH$_3$)—CH=N— or —N=CH—(CH$_3$)=CH— and R$_3$ is as defined in claim 1; or a pharmaceutically acceptable acid additional salt thereof.

7. A compound in accordance with claim 1 having the formula 15a:

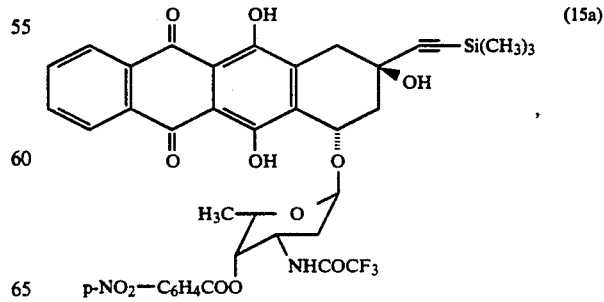
(15a)

8. A compound in accordance with claim 1 having the formula:

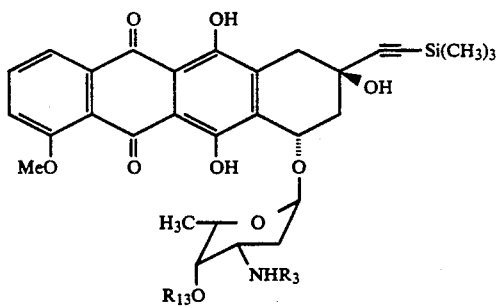

wherein $R_3$ and $R_{13}$ are as defined in claim 1.

9. A compound in accordance with claim 1 having the formula:

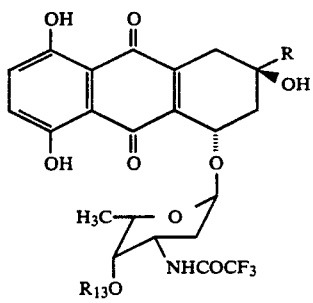

wherein R is —COCH$_3$ or —C≡C—Si(CH$_3$)$_3$ and $R_{13}$ is as defined in claim 1.

10. A compound in accordance with claim 1 having the formula:

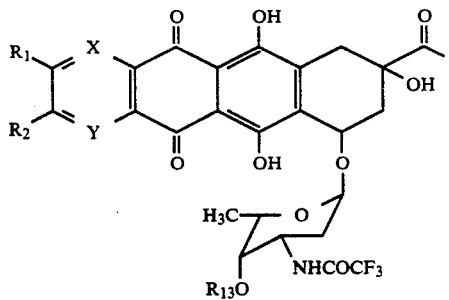

wherein $R_{13}$ is as defined in claim 1, and wherein X=C, Y=N, $R_1$=CH$_3$ and $R_2$=H or X=N, Y=C, $R_1$=H and $R_2$=CH$_3$.

11. A compound in accordance with claim 1 having the formula 44:

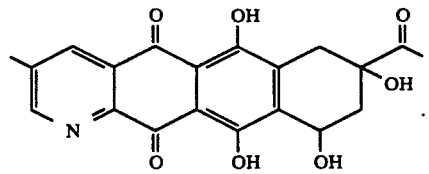

12. A compound in accordance with claim 1 having the formula 46:

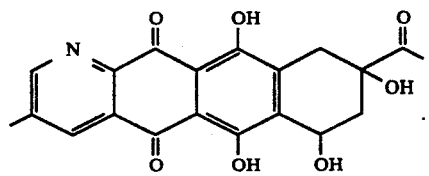

13. A compound in accordance with claim 1 having the formula 13a:

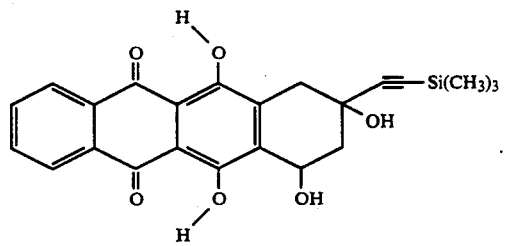

14. A compound in accordance with claim 1 having the formula 27:

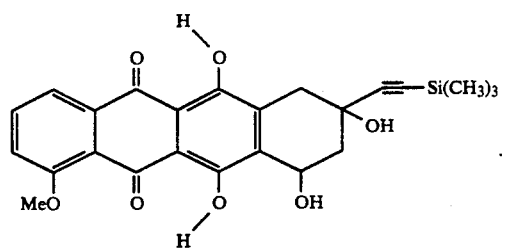

15. A compound in accordance with claim 1 having the formula 33:

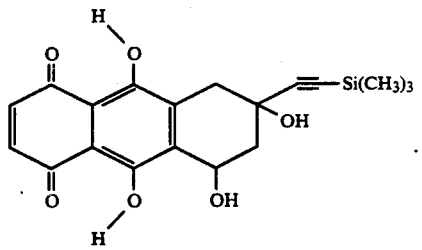

* * * * *